(12) United States Patent
Chen et al.

(10) Patent No.: US 7,326,786 B2
(45) Date of Patent: Feb. 5, 2008

(54) THIAZOLINONE UNSUBSTITUTED QUINOLINES

(75) Inventors: Li Chen, Shanghai (CN); Shaoqing Chen, Bridgewater, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 219 days.

(21) Appl. No.: 11/170,300

(22) Filed: Jun. 29, 2005

(65) Prior Publication Data

US 2006/0004045 A1    Jan. 5, 2006

Related U.S. Application Data

(60) Provisional application No. 60/584,746, filed on Jul. 1, 2004, provisional application No. 60/629,495, filed on Nov. 19, 2004.

(51) Int. Cl.
*C07D 417/06* (2006.01)
(52) U.S. Cl. .................................................... 546/135
(58) Field of Classification Search ................ 546/135; 548/190
See application file for complete search history.

(56) References Cited

FOREIGN PATENT DOCUMENTS

| EP | 1215208 A2 | 6/2002 |
|---|---|---|
| WO | WO 99/65884 A1 | 12/1999 |
| WO | WO 2004/047760 | * 6/2004 |
| WO | WO 2004/047760 A2 | 6/2004 |
| WO | WO 2005/011686 A1 | 2/2005 |

OTHER PUBLICATIONS

Arthur P. Phillips, Journal of the American Chemical Society, vol. 67, pp. 744-748 (1945), XP002354534.

* cited by examiner

*Primary Examiner*—D. Margaret Seaman
*Assistant Examiner*—Nizal S. Chandrakumar
(74) *Attorney, Agent, or Firm*—George W. Johnston; Patricia S. Rocha-Tramaloni; David E. Wildman

(57) ABSTRACT

Thiazolinone quinoline derivatives having no substitution on the quinoline ring active as CDK1 inhibitors which are useful as anti-proliferation agents such as for treating solid tumors.

100 Claims, No Drawings

THIAZOLINONE UNSUBSTITUTED QUINOLINES

PRIORITY TO RELATED APPLICATIONS

This application claims the benefit of Provisional Application(s) Ser. No. 60/584,746, filed Jul. 1, 2004 and Ser. No. 60/629,495, filed Nov. 19, 2004.

FIELD OF THE INVENTION

The field of this invention relates to thiazoline quinoline derivatives where the quinoline ring is unsubstituted, which derivatives demonstrate CDK1 antiproliferative activity and are useful as anti-cancer agents.

BACKGROUND OF THE INVENTION

Cyclin-dependent kinases (CDKs) are serine-threonine protein kinases that play critical roles in regulating the transitions between different phases of the cell-cycle, such as the progression from a quiescent stage in $G_1$ (the gap between mitosis and the onset of DNA replication for a new round of cell division) to S (the period of active DNA synthesis), or the progression from $G_2$ to M phase, in which active mitosis and cell-division occurs. (See, e.g., the articles compiled in *Science*, 274:1643-1677 (1996); and *Ann. Rev. Cell Dev. Biol.*, 13:261-291 (1997)). CDK complexes are formed through association of a regulatory cyclin subunit (e.g., cyclin A, B1, B2, D1, D2, D3 and E) and a catalytic kinase subunit (e.g., CDK1, CDK2, CDK4, CDK5 and CDK6). As the name implies, the CDKs display an absolute dependence on the cyclin subunit in order to phosphorylate their target substrates, and different kinase/cyclin pairs function to regulate progression through specific phases of the cell-cycle.

As seen above, these protein kinases are a class of proteins (enzymes) that regulate a variety of cellular functions. This is accomplished by the phosphorylation of specific amino acids on protein substrates resulting in conformational alteration of the substrate protein. The conformational change modulates the activity of the substrate or its ability to interact with other binding partners. The enzyme activity of the protein kinase refers to the rate at which the kinase adds phosphate groups to a substrate. It can be measured, for example, by determining the amount of a substrate that is converted to a product as a function of time. Phosphorylation of a substrate occurs at the active-site of a protein kinase.

In view of the above properties, these kinases play an important part in the propagation of growth factor signal transduction that leads to cellular proliferation, differentiation and migration. Fibroblast growth factor (FGF) and vascular endothelial growth factor (VEGF) have been recognized as important mediators of tumor promoted angiogenesis. VEGF activates endothelial cells by signaling through two high affinity receptors, one of which is the kinase insert domain-containing receptor (KDR). (See, Hennequin L. F. et. al., *J. Med. Chem.* 45(6):1300 (2002). FGF activates endothelial cells by signaling through the FGF receptor (FGFR). Solid tumors depend upon the formation of new blood vessels (angiogenesis) to grow. Accordingly, inhibitors of the receptors FGFR and KDR that interfere with the growth signal transduction, and thus slow down or prevent angiogenesis, are useful agents in the prevention and treatment of solid tumors. (See, Klohs W. E. et. al., *Current Opinion in Biotechnology*, 10:544 (1999)).

Because CDKs such as CDK1 serve as general activators of cell division, inhibitors of CDK1 can be used as antiproliferative agents. These inhibitors can be used for developing therapeutic intervention in suppressing deregulated cell cycle progression.

SUMMARY OF THE INVENTION

In accordance with this invention, it has been discovered that the compound of the formula:

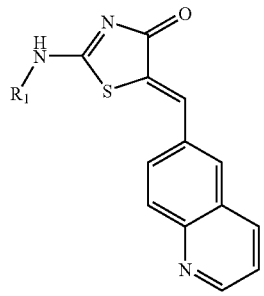

I wherein
$R_1$ is selected from lower alkyl, lower alkoxy, aryloxy-lower alkyl, hydroxy lower alkyl, lower alkoxy lower alkyl, and $R_2$—$(X)_n$—;
X is selected from lower alkylene, cyclo lower alkylene, aryl substituted lower alkylene, carboxy substituted lower alkylene, hydroxy substituted lower alkylene, amido substituted lower alkylene, mono- or di-halo substituted lower alkylene, amino substituted lower alkylene, mono- or di-lower alkyl amino substituted lower alkylene and imido substituted lower alkylene,
$R_2$ is

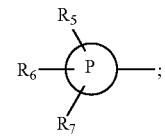

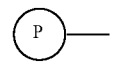

is a carbon containing ring attached through its carbon atom, which ring is selected from an aryl ring, cycloalkyl ring containing from 2 to 6 carbon atoms, a 4 to 6 membered heterocycloalkyl ring containing from 3 to 4 carbon atoms and from 1 to 2 hetero atoms selected from the group consisting of oxygen, nitrogen and sulfur, or a 4 to 6 membered heteroaromatic ring containing from 1 to 2 hetero atoms selected from the group consisting of oxygen, sulfur and nitrogen;
$R_5$, $R_6$ and $R_7$ are independently selected from the group consisting of hydroxy, —$SO_2$, hydroxy-lower alkyl, hydrogen, lower alkyl, halogen, lower alkoxy, amino, and mono- or di-lower alkyl amino, or when two of the substituents $R_5$, $R_6$ and $R_7$ are substituted on adjacent carbon atoms on ring (P), these two substituents can be taken together with their adjacent, attached carbon atoms to form an aryl ring, a 3 to 6 membered cyclic lower alkyl ring, a 4 to 6 membered heterocycloalkyl ring or a 4 to 6 membered heteroaromatic ring with said heterocycloalkyl ring and said heteroaromatic ring containing from 1 to 2 hetero atoms selected from the group consisting of oxygen, nitrogen or sulfur, and n is an integer from 0 to 1; with the proviso that when (P) is an aryl ring, then n is 1 and with the further proviso that when Ⓟ is an aryl ring, n is 1 and X is lower alkylene then one of $R_5$, $R_6$ and $R_7$ is other than hydrogen, halogen, lower alkyl or $SO_2$, and with the still further proviso that when Ⓟ is a cycloalkyl ring and n is 0, then one $R_5$, $R_6$ and $R_7$ is other than hydrogen or lower alkyl;

or N-oxides of compounds where $R_2$ contains a nitrogen in the heterocycloalkyl ring or heteroaromatic ring, sulfones where $R_2$ contains a sulfur in the heterocycloalkyl ring or heteroaromatic ring, or pharmaceutically acceptable salts thereof, inhibit the activity of CDKs, particularly, CDK1. These inventive agents and pharmaceutical compositions containing such agents are useful in treating various diseases or disorder states associated with uncontrolled or unwanted cellular proliferation, such as cancer, autoimmune diseases, viral diseases, fungal diseases, neurodegenerative disorders and cardiovascular diseases.

Inhibiting and/or modulating the activity of CDKs, particularly CDK1, makes these compounds of formula I and compositions containing these compounds useful in treating diseases medicated by kinase activity, particularly as anti-tumor agents in treating cancers.

DETAILED DESCRIPTION OF THE INVENTION

As pointed out herein, the compounds of formula I are potential anti-proliferation agents and are useful for mediating and/or inhibiting the activity of CDKs, particularly CDK1, thus providing anti-tumor agents for treatment of cancer or other diseases associated with uncontrolled or abnormal cell proliferation.

Among the preferred compounds of formula I are:
Compounds of the formula:

I-A

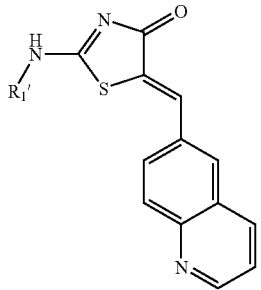

wherein
$R_1'$ is selected from lower alkyl, lower alkoxy, hydroxy lower alkyl, lower alkoxy lower alkyl and phenoxy lower alkyl; or
pharmaceutically acceptable salts thereof;
Compounds of the formula:

I-B

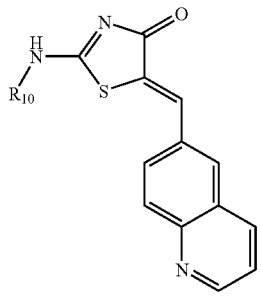

wherein $R_{10}$ is

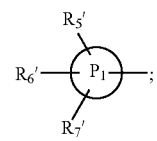

is a cycloalkyl ring containing from 3 to 6 carbon atoms;
$R_5'$ is selected from hydroxy, $SO_2$, hydroxy-lower alkyl, amino, halogen, lower alkoxy, and mono- or di-lower alkyl amino; and
$R'_6$ and $R'_7$ are independently selected from hydroxy, $-SO_2$, hydroxy-lower alkyl, amino, hydrogen, lower alkyl, halogen, lower alkoxy, and mono- or di-lower alkyl amino, or
when two of the substituents $R_5'$, $R_6'$ and $R_7'$ are substituents on adjacent carbon atoms on ring

these two substituents can be taken together with their adjacent, attached carbon atoms to form a group selected from an aryl ring, a 3 to 6 membered cycloalkyl ring, a 4 to 6 membered heterocycloalkyl ring and a 4 to 6 membered heteroaromatic ring with said heterocycloalkyl ring and said heteroaromatic ring containing from 1 to 2 hetero atoms selected from oxygen, nitrogen, and sulfur; or
N-oxides of compounds where $R_{10}$ contains a nitrogen in the heterocycloalkyl ring or heteroaromatic ring, sulfones where $R_{10}$ contains a sulfur in the heterocycloalkyl ring or heteroaromatic ring; or
pharmaceutically acceptable salts thereof;
Compounds of the formula:

I-C

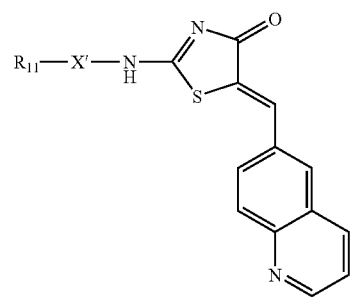

wherein

X' is lower alkylene and $R_{11}$ is

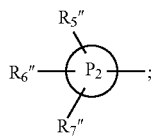

is an aryl ring;

$R_5''$ is selected from hydroxy, hydroxy-lower alkyl, amino, lower alkoxy and mono or di lower alkyl amino; and $R_6''$ and $R_7'$ are selected from hydroxy, hydroxy-lower alkyl, amino, hydrogen, lower alkyl, halogen, lower alkoxy and mono- or di-lower alkyl amino, or when two of the substituents $R_5''$ $R_6''$ and $R_7''$ are substituted on adjacent carbon atoms on ring

these two substituents can be taken together with their adjacent, attached carbon atoms to form a group selected from an aryl ring, a 3 to 6 membered cycloalkyl ring, a 4 to 6 membered heterocycloalkyl ring and a 4 to 6 membered heteroaromatic ring with said heterocycloalkyl ring and said heteroaromatic ring containing from 1 to 2 hetero atoms selected from oxygen, nitrogen and sulfur; or N-oxides of compounds where $R_{11}$ contains a nitrogen in the heterocycloalkyl ring or heteroaromatic ring, sulfones where $R_{11}$ contains a sulfur in the heterocycloalkyl ring or heteroaromatic ring; or pharmaceutically acceptable salts thereof;

Compounds of the formula:

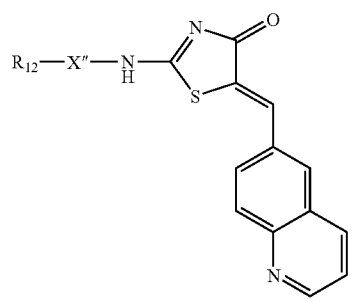

I-D wherein $R_{12}$ is

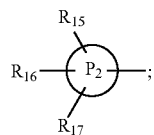

is an aryl ring; X" is selected from hydroxy-lower alkylene, cyclo lower alkylene, aryl lower alkylene, mono- or di-halo lower alkylene, amino lower alkylene, mono- or di-lower alkyl amino lower alkylene and imido lower alkylene, $R_{15}$, $R_{16}$ and $R_{17}$ are independently selected from hydroxy, $—SO_2$, hydroxy-lower alkyl, amino, hydrogen, lower alkyl, halogen, lower alkoxy, and mono- or di-lower alkyl amino, or when two of the substituents $R_{15}$, $R_{16}$ and $R_{17}$ are substituted on adjacent carbon atoms on ring

these two substituents can be taken together with their adjacent, attached carbon atoms to form a group selected from an aryl ring, a 3 to 6 membered cycloalkyl ring, a 4 to 6 membered heterocycloalkyl ring or a 4 to 6 membered heteroaromatic ring with said heterocycloalkyl ring and said heteroaromatic ring containing from 1 to 2 hetero atoms selected from the group consisting of oxygen, nitrogen or sulfur; or N-oxides of compounds where $R_{12}$ contains a nitrogen in the heterocycloalkyl ring or heteroaromatic ring, sulfones where $R_{12}$ contains a sulfur in the heterocycloalkyl ring or heteroaromatic ring; or pharmaceutically acceptable salts thereof.

Compounds of the formula:

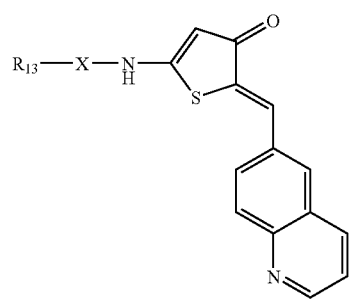

I-E wherein X is as above;

$R_{13}$ is

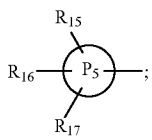

is a carbon containing ring attached through its carbon atom, which ring is selected from cycloalkyl ring containing from 2 to 6 carbon atoms, a 4 to 6 membered heterocycloalkyl ring containing from 3 to 5 carbon atoms and from 1 to 2 hetero atoms selected from oxygen, nitrogen and sulfur, and a 4 to 6 membered heteroaromatic ring containing from 1 to 2 hetero atoms selected from oxygen, sulfur, and nitrogen; and $R_{15}$, $R_{16}$ and $R_{17}$ are as above; or N-oxides of compounds where $R_{13}$ contains a nitrogen in the heterocycloalkyl ring or heteroaromatic ring, sulfones where $R_{13}$ contains a sulfur in the heterocycloalkyl ring or heteroaromatic ring; or pharmaceutically acceptable salts thereof.

Compounds of the formula:

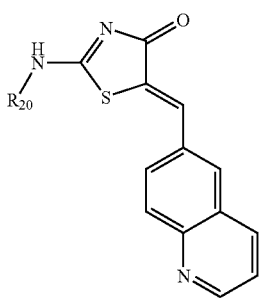

I-F wherein $R_{20}$ is

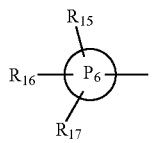

is a carbon containing ring attached through its carbon atom, which ring is selected from a 4 to 6 membered heterocycloalkyl ring containing from 3 to 4 carbon atoms and from 1 to 2 hetero atoms, nitrogen and sulfur, and a 5 or 6 membered heteroaromatic ring, wherein the heteroaromatic and heterocycloalky ring contain from 1 to 2 hetero atoms selected from oxygen, sulfur and nitrogen; and $R_{15}$, $R_{16}$ and $R_{17}$ are as above; or N-oxides of compounds where $R_{20}$ contains a nitrogen in the heterocycloalkyl ring or heteroaromatic ring, sulfones where $R_{20}$ contains a sulfur in the heterocycloalkyl ring or heteroaromatic ring;

or pharmaceutically acceptable salts thereof.

In compounds I where $R_1$, $R_{10}$, $R_{11}$, $R_{12}$, $R_{13}$ and $R_{20}$ are substituents containing an aryl moiety, the preferred aryl moiety is phenyl. As used herein the halogen includes all four halogens such as chlorine, fluorine, bromine and iodine.

As used in the specification, the term "lower alkyl", alone or in combination, means a monovalent straight or branched-chain saturated hydrocarbon alkyl group containing from one to six carbon atoms, such as methyl, ethyl, n-propyl, isopropyl, n-butyl, sec-butyl, isobutyl, tert-butyl, n-pentyl, n-hexyl and the like.

The term "cycloalkyl" means a cyclo lower alkyl substituent which designates a monovalent unsubstituted 3- to 6-membered saturated carbocylic hydrocarbon ring. Among the preferred cycloalkyl substituents are cyclopropyl, cyclobutyl, cyclohexyl, etc.

The term "lower alkoxy" means a straight-chain or branched-chain alkoxy group formed from lower alkyl containing from one to six carbon atoms, such as methoxy, ethoxy, n-propoxy, isopropoxy, n-butoxy, tert-butoxy and the like.

The term "aryl" means a monovalent mono- or bicyclic unsubstituted aromatic hydrocarbon ring, such as phenyl or naphthyl, with phenyl being preferred.

The term "heterocycloalkyl" refers to a 4 to 6 membered monocyclic saturated ring containing 3 to 5 carbon atoms and one or two hetero atoms selected from the group consisting of oxygen, nitrogen or sulfur. Among the preferred heterocyclic alkyl groups are included mopholinyl, thiopyranyl or tetrahydropyranyl.

The term "heteroaromatic ring" refers to a monovalent 4 to 6 membered monocyclic heteroaromatic ring containing from 3 to 5 carbon atoms and from 1 to 2 hetero atoms selected from the group consisting of oxygen, nitrogen or sulfur. Among the preferred heteroaromatic groups are included thiophenyl, thioazole, pyridinyl, furanyl, etc.

The term "lower alkylene" designates a divalent saturated straight or branch chain hydrocarbon substituent containing from one to six carbon atoms.

The term "carboxy substituted lower alkylene" denotes a lower alkylene substituent as designated hereinbefore substituted, preferably monosubstituted, with a carboxy radical.

The term "hydroxy substituted lower alkylene" designates a lower alkylene substituent substituted, preferably monosubstituted, with a hydroxy group. Where an amido substituted lower alkylene is used, this designates a lower alkylene substituent as set forth hereinbefore substituted with an amido substituent.

The term "mono- or di-halo substituted lower alkylene substituents" designate a lower alkylene substituent which is either mono-substituted or di-substituted on one or two carbon atoms of the lower alkylene chain.

The term "amino substituted lower alkylene" designates a lower alkylene substituent which is substituted, preferably monosubstituted, with an amino group. The term amino substituted lower alkylene designates that the amino group on the amino lower alkylene may be substituted by 1 or 2 lower alkyl groups. In the case of one lower alkyl group substitution, the term "mono-lower alkyl amino" is used. In the case of two lower alkyl substituents on the nitrogen atom of the amine group, the substituent is a "di-lower alkyl amino group."

The term "amido substituted lower alkylene" designates a lower alkylene substituent as hereinbefore defined substituted on one position with an amido group."

The term "aryloxy" designates an aryloxy substituent where aryl is as above. The preferred aryl group is phenyl and the preferred aryloxy is phenoxy.

The term "pharmaceutically acceptable salts" refers to conventional acid-addition salts that retain the biological effectiveness and properties of the compounds of formulas I, II, III, IV and V and are formed from suitable non-toxic organic or inorganic acids. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. The chemical modification of a pharmaceutical compound (i.e., drug) into a salt is a technique well known to pharmaceutical chemists to obtain improved physical and chemical stability, hygroscopicity, flowability and solubility of compounds. See, e.g., H. Ansel et al., *Pharmaceutical Dosage Forms and Drug Delivery Systems* (6th Ed. 1995) at pp. 196 and 1456-1457.

In accordance with this invention, the compounds of formula I can be prepared from a compound of the formula:

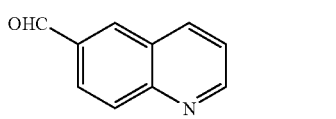

II

The compound of formula II is converted to the compound of formula I via the following reaction scheme.

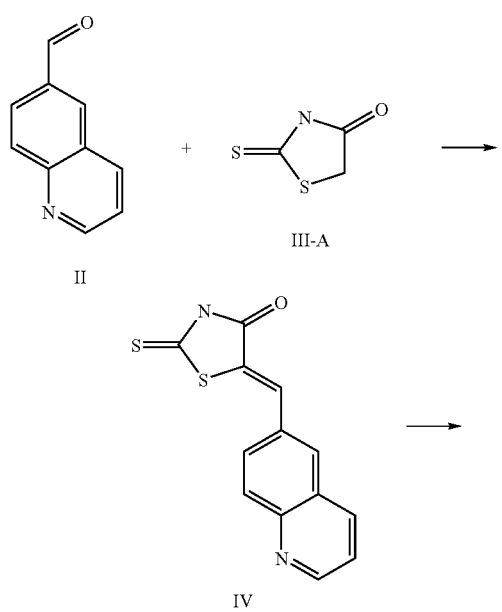

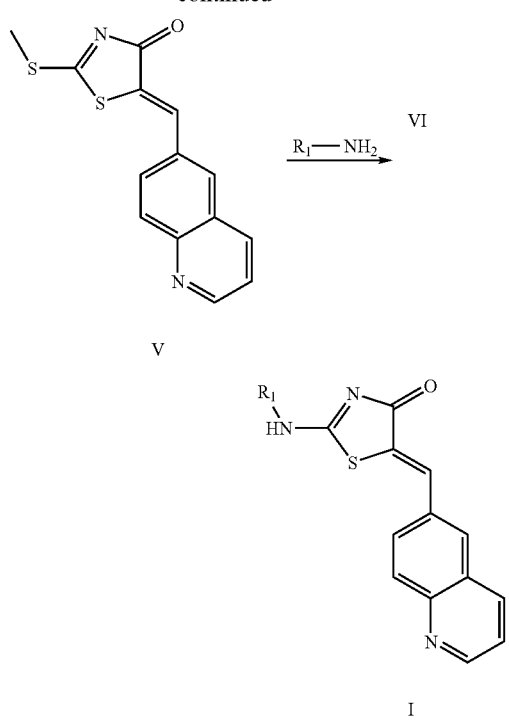

wherein

R$_1$ is as above.

In accordance with this invention, the compound of formula II is reacted with the compound of formula III-A (rhodanine (2-thioxo-4-thiazolidinone)) via a Knoevenegel reaction to produce the compound of formula IV. Any of the conditions conventional in carrying out Knoevenegel reaction can be utilized in carrying out this condensation. Generally, this reaction is carried out at reflux temperature in the presence of alkali metal acetate and acetic acid. In the next step of this synthesis, the resulting substituted thiazolidine of formula IV is treated with a methylating agent to methylate the thio group on the compound of formula IV to produce the compound of formula V. The preferred methylating agent is iodomethane. This reaction is carried out in an organic amine base such as diisopropylethylamine (DIEA). In carrying out this reaction, temperature and pressure are not critical and this reaction can be carried out at room temperature and atmospheric pressure. In fact, in carrying out this reaction, any of the conditions conventional in methylating a thio group can be used.

In the next step of this synthesis, the compound of formula V is reacted with the compound of formula VI to produce the compound of formula I. The compound of formula VI is an amine and any means conventionally used in amine substitution of a methylthio group can be used in carrying out this reaction. In accordance with one embodiment, this substitution is carried out by reacting the compound of formula VI with the compound of formula V in the presence of a conventional solvent such as acetonitrile. Generally, this reaction is carried out in the presence of an amine base such as diisopropylethylamine.

On the other hand, the compound of formula I can be prepared by reacting the compound of formula II with a compound of the formula:

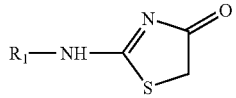

VII

The reaction of the compound of formula VII with the compound of formula II using Knoevenegal condensation to produce the compound of formula I, is carried out in an organic solvent such as benzene or toluene at high temperature of from 100° C. to 200° C. in a closed system. In this manner, this reaction is carried out under high temperatures and pressure. The compound of formula VII can be directly formed by direct replacement through reacting the compound of the formula

 VI wherein R1 is as above, with a compound of the formula III-A. The replacement reaction is generally carried out in the presence of mercuric chloride. This reaction is carried out in an inert organic solvent. Any conventional inert organic solvent such as acetonitrile, methylene chloride, etc. can be utilized. In carrying out this reaction, an amine base, such as diisoproprylethylamine, is used. In carrying out this reaction, temperature and pressure are not critical and this reaction can be carried out at room temperature and atmospheric pressure. In carrying out this reaction, any conventional method of replacing a mercapto group with an amine can be utilized.

In the compound of formula VI where $R_1$ is $R_2X$, where $R_2$ is as above and X is a hydroxy lower alkylene, these compounds can be prepared from the corresponding amino acids or amino acid esters by reduction with an alkali metal borohydride. On the other hand, these hydroxy lower alkylene compounds can be prepared for the corresponding cyano carboxylic acid esters by reduction with lithium aluminum hydride. Reduction reduces the cyano group to an amino group and the ester to a hydroxy group. This reduction should take place before reacting the compound of formula VI with the compound of formula V.

On the other hand, where in the compound of formula VI, $R_1$ is $R_2X$— and X is a carboxy lower alkylene, amido lower alkylene or imido lower alkylene, these compounds can be directly converted to the compound of formula I by reacting the corresponding compound of formula VI with the compound of formula V or the compound of formula III-A as described above.

In the compounds of Formula I, N-oxides can be formed from a nitrogen atom in a nitrogen containing ring in the substituent which either is contained in the ring Ⓟ or formed by the substituents $R_5$, $R_6$ and $R_7$. These N-oxides can be produced from such a tertiary ring nitrogen atom by oxidation. Any conventional method of oxidizing a tertiary nitrogen atom to an N-oxide can be utilized. The preferred oxidizing agent is metachloroperbenzoic acid (MCPBA).

Pharmaceutical compositions according to the invention may, alternatively or in addition to a compound of Formula I, comprise as an active ingredient pharmaceutically acceptable prodrugs, pharmaceutically active metabolites, and pharmaceutically acceptable salts of such compounds and metabolites. Such compounds, prodrugs, multimers, salts, and metabolites are sometimes referred to herein collectively as "active agents" or "agents."

In the case of agents that are solids, it is understood by those skilled in the art that the inventive compounds and salts may exist in different crystal or polymorphic forms, all of which are intended to be within the scope of the present invention and specified formulas.

Therapeutically effective amounts of the active agents of the invention may be used to treat diseases mediated by modulation or regulation of the protein kinases CDK1. An "effective amount" is intended to mean that amount of an agent that significantly inhibits proliferation and/or prevents de-differentiation of a eukaryotic cell, e.g., a mammalian, insect, plant or fungal cell, and is effective for the indicated utility, e.g., specific therapeutic treatment.

The amount of a given agent that will correspond to such an amount will vary depending upon factors such as the particular compound, disease condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. "Treating" is intended to mean at least the mitigation of a disease condition in a subject such as mammal (e.g., human), that is affected, at least in part, by the activity of CDK1 protein kinase includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

The present invention is further directed to methods of modulating or inhibiting protein kinase CDK1 activity, for example in mammalian tissue, by administering the inventive agent. The activity of agents as anti-proliferatives is easily measured by known methods, for example by using whole cell cultures in an MTT assay. The activity of the inventive agents as modulators of CDK1 protein kinase activity may be measured by any of the methods available to those skilled in the art, including in vivo and/or in vitro assays. Examples of suitable assays for activity measurements include those described in International Publication No. WO 99/21845; Parast et al., Biochemistry, 37, 16788-16801 (1998); Connell-Crowley and Harpes, Cell Cycle: Materials and Methods, (Michele Pagano, ed. Springer, Berlin, Germany) (1995); International Publication No. WO 97/34876; and International Publication No. WO 96/14843. These properties may be assessed, for example, by using one or more of the biological testing procedures set out in the examples below.

The active agents of the invention may be formulated into pharmaceutical compositions as described below. Pharmaceutical compositions of this invention comprise an effective modulating, regulating, or inhibiting amount of a compound of formula I and an inert, pharmaceutically acceptable carrier or diluent. In one embodiment of the pharmaceutical compositions, efficacious levels of the inventive agents are provided so as to provide therapeutic benefits involving anti-proliferative ability. By "efficacious levels" is meant levels in which proliferation is inhibited, or controlled. These compositions are prepared in unit-dosage form appro priate for the mode of administration, e.g., parenteral or oral administration.

An inventive agent can be administered in conventional dosage form prepared by combining a therapeutically effective amount of an agent (e.g., a compound of formula I) as an active ingredient with appropriate pharmaceutical carriers or diluents according to conventional procedures. These procedures may involve mixing, granulating and compressing or dissolving the ingredients as appropriate to the desired preparation.

The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methyl methacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent can be dissolved in an aqueous solution of an organic or inorganic acid. If a soluble salt form is not available, the agent may be dissolved in a suitable cosolvent or combinations of cosolvents.

It will be appreciated that the actual dosages of the agents used in the compositions of this invention will vary according to the particular complex being used, the particular composition formulated, the mode of administration and the particular site, host and disease being treated. Optimal dosages for a given set of conditions can be ascertained by those skilled in the art using conventional dosage determination tests in view of the experimental data for an agent.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

For oral administration, the compounds can be formulated readily by combining the compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores.

EXAMPLES

Example 1

2-[(Thiophen-2-ylmethyl)-amino]-5-[1-quinolin-6-yl-meth-(Z)-ylidene]-thiazol-4-one

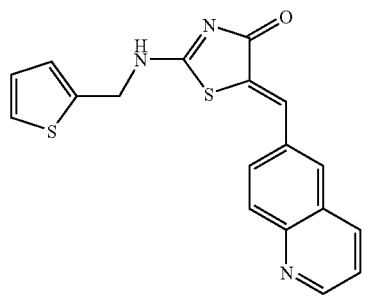

a) Preparation of 2-methylsulfanyl-5-[1-quinolin-6-yl-meth-(Z)-ylidene]-thiazol-4-one

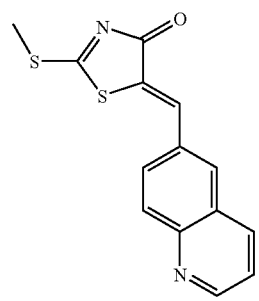

The suspension of 6-quinolinecarboxaldehyde (6 g, 38 mmol), rhodanine (2-thioxo-4-thiazolidinone) (5.08 g, 38 mmol) and sodium acetate (12.5 g, 152 mmol) in acetic acid (50 mL) was stirred under reflux for 12 h. After cooling to room temperature, water (150 mL) was added. The solid was collected by filtration, washed with water and dried to obtain 5-[1-quinolin-6-yl-meth-(Z)-ylidene]-2-thioxo-thiazolidin-4-one (10.2 g, 98%) as a yellow solid. LC-MS m/e 273 (MH$^+$).

The suspension of 5-[1-quinolin-6-yl-meth-(Z)-ylidene]-2-thioxo-thiazolidin-4-one (10.2 g, 37.5 mmol), iodomethane (4.65 mL, 75 mmol) and DIEA (N,N-diisopropylethylamine) (9.8 mL, 56.3 mmol) in anhydrous ethanol (100 mL) was stirred at room temperature for 12 h. After adding water (200 mL), the solid was collected by filtration, washed with water and dried to obtain 2-methylsulfanyl-5-[1-quinolin-6-yl-meth-(Z)-ylidene]-thiazol-4-one (8.76 g, 82%) as a grey solid. LC-MS m/e 287 (MH$^+$).

b) Preparation of 2-[(thiophen-2-ylmethyl)-amino]-5-[1-quinolin-6-yl-meth-(Z)-ylidene]-thiazol-4-one The suspension of 2-methylsulfanyl-5-[1-quinolin-6-yl-meth-(Z)-ylidene]-thiazol-4-one (example 1a, 3.0 g, 10.5 mmol), thiophene methyl amine (2.4 g, 21.0 mmol) and diisopropylethylamine (DIEA) (3.66 mL, 21.0 mmol) in acetonitrile (30 mL) was stirred under at 80° C. for 12 h.

After cooling to room temperature, the solid was collected by filtration, washed with a little bit of acetonitrile and dried. Flash chromatography (Merck Silica gel 60, 230-400 mesh, 0%-10% methanol in methylene chloride in 30 min) afforded 2-[(thiophen-2-ylmethyl)-amino]-5-[1-quinolin-6-yl-meth-(Z)-ylidene]-thiazol-4-one (2.5 g, 67%) as a light yellow solid: LC-MS m/e 352 (MH$^+$).

Example 2

2-Pentylamino-5-[1-quinolin-6-yl-meth-(Z)-ylidene]-thiazol-4-one

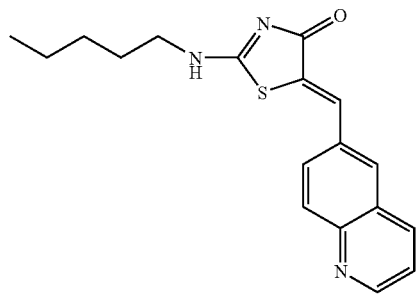

Similar procedure as described in example 1b was used, starting from 2-methylsulfanyl-5-[1-quinolin-6-yl-meth-(Z)-ylidene]-thiazol-4-one, pentylamine and DIEA to give 2-pentylamino-5-[1-quinolin-6-yl-meth-(Z)-ylidene]-thiazol-4-one. LC-MS m/e 326 (MH$^+$).

Example 3

2-[2-(4-Methoxy-phenyl)-ethylamino]-5-[1-quinolin-6-yl-meth-(Z)-ylidene]-thiazol-4-one

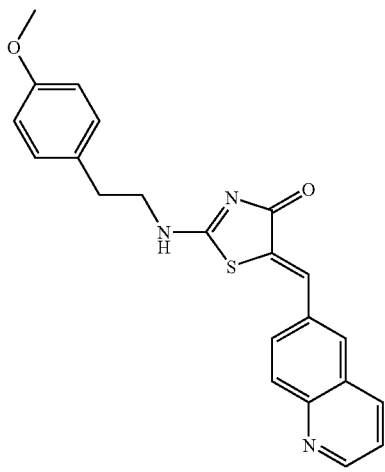

Similar procedure as described in example 1b was used, starting from 2-methylsulfanyl-5-[1-quinolin-6-yl-meth-(Z)-ylidene]-thiazol-4-one, 4-methoxy-phenyl-ethyl amine and DIEA to give 2-[2-(4-methoxy-phenyl)-ethylamino]-5-[1-quinolin-6-yl-meth-(Z)-ylidene]-thiazol-4-one. LC-MS m/e 390 (MH$^+$).

Example 4

2-[2-(3-Methoxy-phenyl)-ethylamino]-5-[1-quinolin-6-yl-meth-(Z)-ylidene]-thiazol-4-one

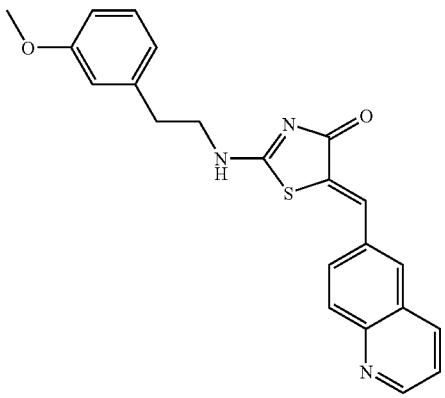

Similar procedure as described in example 1b was used, starting from 2-methylsulfanyl-5-[1-quinolin-6-yl-meth-(Z)-ylidene]-thiazol-4-one, 2-(3-Methoxy-phenyl)-ethyl amine and DIEA to give 2-[2-(3-methoxy-phenyl)-ethylamino]-5-[1-quinolin-6-yl-meth-(Z)-ylidene]-thiazol-4-one. LC-MS m/e 390 (MH$^+$).

Example 5

2-[2-(2,5-Dimethoxy-phenyl)-ethylamino]-5-[1-quinolin-6-yl-meth-(Z)-ylidene]-thiazol-4-one

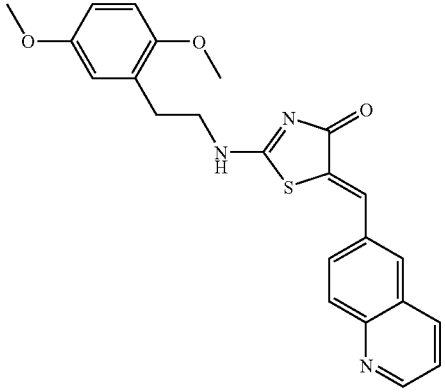

Similar procedure as described in example 1b was used, starting from 2-methylsulfanyl-5-[1-quinolin-6-yl-meth-(Z)-ylidene]-thiazol-4-one, 2-(2,5-dimethoxy-phenyl ethylamine and DIEA to give 2-[2-(2,5-dimethoxy-phenyl)-ethylamino]-5-[1-quinolin-6-yl-meth-(Z)-ylidene]-thiazol-4-one. LC-MS m/e 378 (MH$^+$).

Example 6

2-[(Furan-2-ylmethyl)-amino]-5-[1-quinolin-6-yl-meth-(Z)-ylidene]-thiazol-4-one

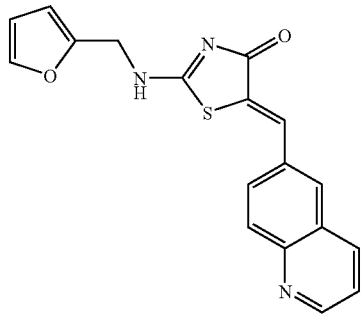

Similar procedure as described in example 1b was used, starting from 2-methylsulfanyl-5-[1-quinolin-6-yl-meth-(Z)-ylidene]-thiazol-4-one, furfurylamine and DIEA to give 2-[(furan-2-ylmethyl)-amino]-5-[1-quinolin-6-yl-meth-(Z)-ylidene]-thiazol-4-one LC-MS m/e 336 (MH$^+$).

Example 7

2-[(2,3-Dihydro-benzofuran-5-ylmethyl)-amino]-5-[1-quinolin-6-yl-meth-(Z)-ylidene]-thiazol-4-one

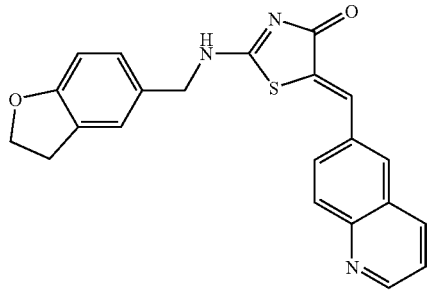

Similar procedure as described in example 1b was used, starting from 2-methylsulfanyl-5-[1-quinolin-6-yl-meth-(Z)-ylidene]-thiazol-4-one, (2,3-Dihydro-benzofuran-5-yl-methyl) amine and DIEA to give 2-[(2,3-dihydro-benzofuran-5-ylmethyl)-amino]-5-[1-quinolin-6-yl-meth-(Z)-ylidene]-thiazol-4-one. LC-MS m/e 388 (MH$^+$).

Example 8

2-[(Benzo[1,3]dioxol-5-ylmethyl)-amino]-5-[1-quinolin-6-yl-meth-(Z)-ylidene]-thiazol-4-one

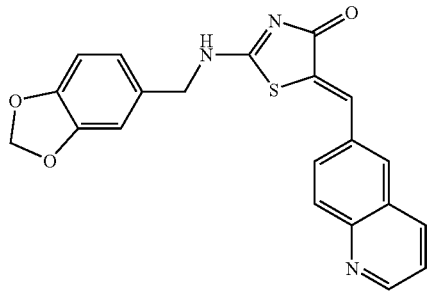

Similar procedure as described in example 1b was used, starting from 2-methylsulfanyl-5-[1-quinolin-6-yl-meth-(Z)-ylidene]-thiazol-4-one, benzo[1,3]dioxol-5-ylmethyl amine and DIEA to give 2-[(benzo[1,3]dioxol-5-ylmethyl)-amino]-5-[1-quinolin-6-yl-meth-(Z)-ylidene]-thiazol-4-one. LC-MS m/e 390 (MH$^+$).

Example 9

2-[2-(2-Ethoxy-phenyl)-ethylamino]-5-[1-quinolin-6-yl-meth-(Z)-ylidene]-thiazol-4-one

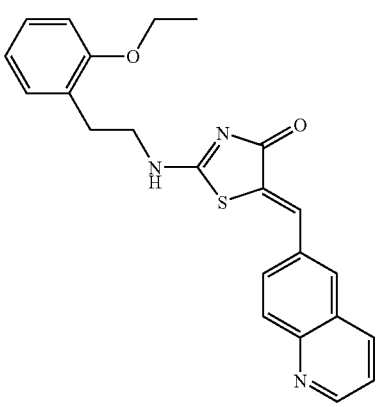

Similar procedure as described in example 1b was used, starting from 2-methylsulfanyl-5-[1-quinolin-6-yl-meth-(Z)-ylidene]-thiazol-4-one, 2-(2-Ethoxy-phenyl)-ethylamine and DIEA to give 2-[2-(2-ethoxy-phenyl)-ethylamino]-5-[1-quinolin-6-yl-meth-(Z)-ylidene]-thiazol-4-one. LC-MS m/e 404 (MH$^+$).

Example 10

2-(2-Methoxy-benzylamino)-5-[1-quinolin-6-yl-meth-(Z)-ylidene]-thiazol-4-one

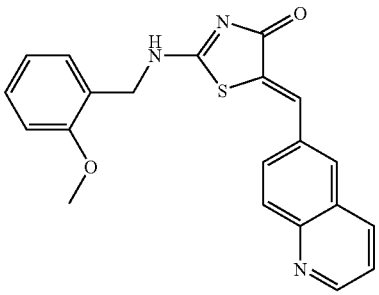

Similar procedure as described in example 1b was used, starting from 2-methylsulfanyl-5-[1-quinolin-6-yl-meth-(Z)-ylidene]-thiazol-4-one, 2-methoxy-benzylamine and DIEA to give 2-(2-methoxy-benzylamino)-5-[1-quinolin-6-yl-meth-(Z)-ylidene]-thiazol-4-one. LC-MS m/e 376 (MH$^+$).

Example 11

2-[2-(2-Methoxy-phenyl)-ethylamino]-5-[1-quinolin-6-yl-meth-(Z)-ylidene]-thiazol-4-one

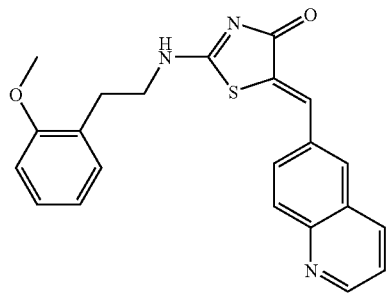

Similar procedure as described in example 1b was used, starting from 2-methylsulfanyl-5-[1-quinolin-6-yl-meth-(Z)-ylidene]-thiazol-4-one, 2-(2-methoxy-phenyl)-ethylamine and DIEA to give 2-[2-(2-methoxy-phenyl)-ethylamino]-5-[1-quinolin-6-yl-meth-(Z)-ylidene]-thiazol-4-one. LC-MS m/e 390 (MH$^+$).

Example 12

2-((S)-1-Hydroxymethyl-2-phenyl-ethylamino)-5-[1-quinolin-6-yl-meth-(Z)-ylidene]-thiazol-4-one

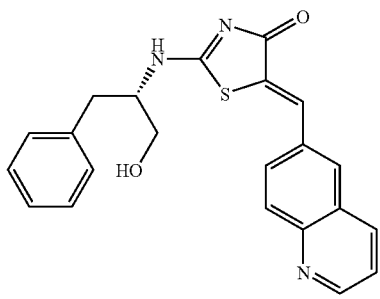

Similar procedure as described in example 1b was used, starting from 2-methylsulfanyl-5-[1-quinolin-6-yl-meth-(Z)-ylidene]-thiazol-4-one, (S)-1-hydroxymethyl-2-phenyl-ethylamine and DIEA to give 2-((S)-1-hydroxymethyl-2-phenyl-ethylamino)-5-[1-quinolin-6-yl-meth-(Z)-ylidene]-thiazol-4-one. LC-MS m/e 390 (MH$^+$).

Example 13

2-(2-Benzo[1,3]dioxol-5-yl-ethylamino)-5-[1-quinolin-6-yl-meth-(Z)-ylidene]-thiazol-4-one

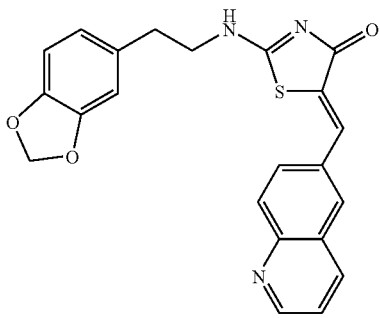

Similar procedure as described in example 1b was used, starting from 2-methylsulfanyl-5-[1-quinolin-6-yl-meth-(Z)-ylidene]-thiazol-4-one, 2-benzo[1,3]dioxol-5-yl-ethylamine and DIEA to give (2-benzo[1,3]dioxol-5-yl-ethylamino)-5-[1-quinolin-6-yl-meth-(Z)-ylidene]-thiazol-4-one. LC-MS m/e 404 (MH$^+$).

Example 14

2-[2-(4-Amino-phenyl)-ethylamino]-5-[1-quinolin-6-yl-meth-(Z)-ylidene]-thiazol-4-one

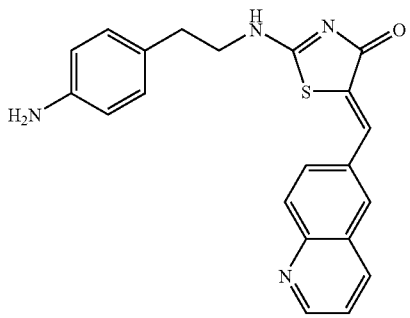

Similar procedure as described in example 1b was used, starting from 2-methylsulfanyl-5-[1-quinolin-6-yl-meth-(Z)-ylidene]-thiazol-4-one, 2-(4-amino-phenyl)-ethylamine and DIEA to give 2-[2-(4-amino-phenyl)-ethylamino]-5-[1-quinolin-6-yl-meth-(Z)-ylidene]-thiazol-4-one. LC-MS m/e 375 (MH$^+$).

Example 15

2-(2-Pyridin-2-yl-ethylamino)-5-[1-quinolin-6-yl-meth-(Z)-ylidene]-thiazol-4-one

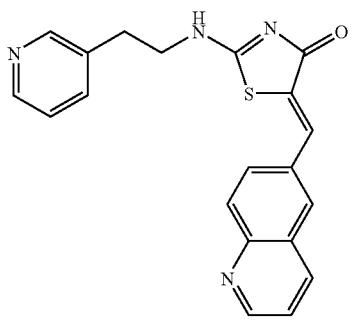

Similar procedure as described in example 1b was used, starting from 2-methylsulfanyl-5-[1-quinolin-6-yl-meth-(Z)-ylidene]-thiazol-4-one, 2-pyridin-2-yl-ethylamine and DIEA to give 2-(2-pyridin-2-yl-ethylamino)-5-[1-quinolin-6-yl-meth-(Z)-ylidene]-thiazol-4-one. LC-MS m/e 361 (MH$^+$).

Example 16

2-(2-Pyridin-3-yl-ethylamino)-5-[1-quinolin-6-yl-meth-(Z)-ylidene]-thiazol-4-one

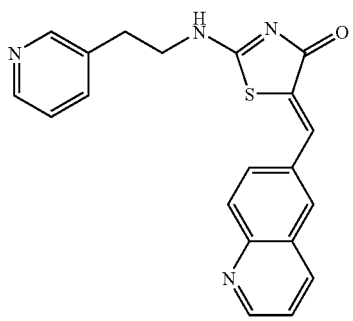

Similar procedure as described in example 1b was used, starting from 2-methylsulfanyl-5-[1-quinolin-6-yl-meth-(Z)-ylidene]-thiazol-4-one, 2-pyridin-3-yl-ethylamine and DIEA to give 2-(2-pyridin-3-yl-ethylamino)-5-[1-quinolin-6-yl-meth-(Z)-ylidene]-thiazol-4-one. LC-MS m/e 361 (MH$^+$).

Example 17

2-(2-thiophen-2-yl-ethylamino)-5-[1-quinolin-6-yl-meth-(Z)-ylidene]-thiazol-4-one

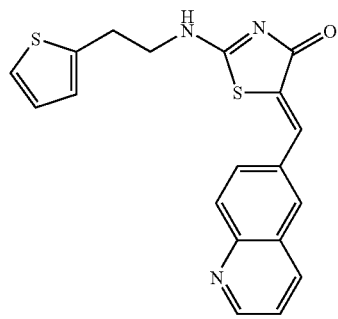

Similar procedure as described in example 1b was used, starting from 2-methylsulfanyl-5-[1-quinolin-6-yl-meth-(Z)-ylidene]-thiazol-4-one, 2-thiophen-2-yl-ethylamine and DIEA to give 2-(2-thiophen-2-yl-ethylamino)-5-[1-quinolin-6-yl-meth-(Z)-ylidene]-thiazol-4-one. LC-MS m/e 366 (MH$^+$).

Example 18

2-[2-(3H-Imidazol-4-yl)-ethylamino]-5-[1-quinolin-6-yl-meth-(Z)-ylidene]-thiazol-4-one

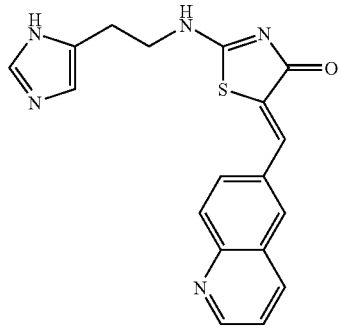

Similar procedure as described in example 1b was used, starting from 2-methylsulfanyl-5-[1-quinolin-6-yl-meth-(Z)-ylidene]-thiazol-4-one, 2-(3H-imidazol-4-yl)-ethylamine and DIEA to give 2-[2-(3H-imidazol-4-yl)-ethylamino]-5-[1-quinolin-6-yl-meth-(Z)-ylidene]-thiazol-4-one. LC-MS m/e 350 (MH$^+$).

Example 19

2-(2-Pyridin-4-yl-ethylamino)-5-[1-quinolin-6-yl-meth-(Z)-ylidene]-thiazol-4-one

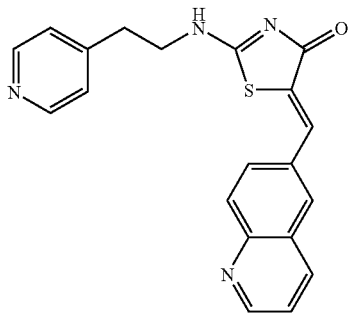

Similar procedure as described in example 1b was used, starting from 2-methylsulfanyl-5-[1-quinolin-6-yl-meth-(Z)-ylidene]-thiazol-4-one, 2-pyridin-4-yl-ethylamine and DIEA to give 2-(2-pyridin-4-yl-ethylamino)-5-[1-quinolin-6-yl-meth-(Z)-ylidene]-thiazol-4-one. LC-MS m/e 361 (MH$^+$).

Example 20

2-((R)-1-Hydroxymethyl-2-phenyl-ethylamino)-5-[1-quinolin-6-yl-meth-(Z)-ylidene]-thiazol-4-one

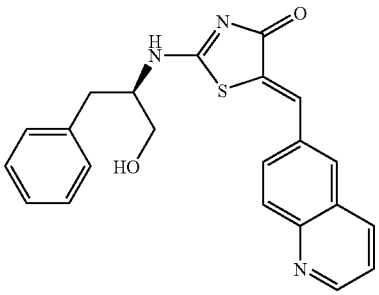

Similar procedure as described in example 1b was used, starting from 2-methylsulfanyl-5-[1-quinolin-6-yl-meth-(Z)-ylidene]-thiazol-4-one, (R)-1-hydroxymethyl-2-phenyl-ethylamine and DIEA to give 2-((R)-1-hydroxymethyl-2-phenyl-ethylamino)-5-[1-quinolin-6-yl-meth-(Z)-ylidene]-thiazol-4-one. LC-MS m/e 390 (MH$^+$).

Example 21

2-(2-Phenoxy-ethylamino)-5-[1-quinolin-6-yl-meth-(Z)-ylidene]-thiazol-4-one

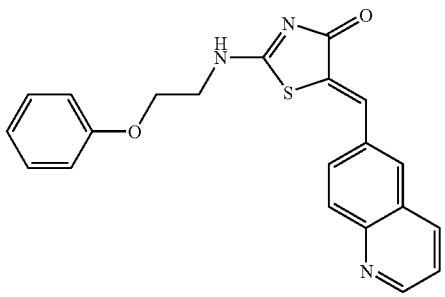

Similar procedure as described in example 1b was used, starting from 2-methylsulfanyl-5-[1-quinolin-6-yl-meth-(Z)-ylidene]-thiazol-4-one, (2-phenoxy-ethylamine and DIEA to give 2-(2-phenoxy-ethylamino)-5-[1-quinolin-6-yl-meth-(Z)-ylidene]-thiazol-4-one. LC-MS m/e 376 (MH$^+$).

Example 22

2-((1R,2S)-2-Phenyl-cyclopropylamino)-5-[1-quinolin-6-yl-meth-(Z)-ylidene]-thiazol-4-one

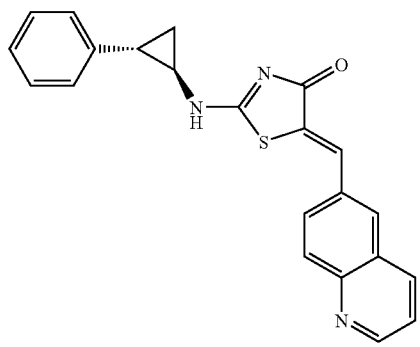

Similar procedure as described in example 1b was used, starting from 2-methylsulfanyl-5-[1-quinolin-6-yl-meth-(Z)-ylidene]-thiazol-4-one, trans-2-phenyl-cyclopropylamine hydrochloride and DIEA to give 2-((1R,2S)-2-phenyl-cyclopropylamino)-5-[1-quinolin-6-yl-meth-(Z)-ylidene]-thiazol-4-one. LC-MS m/e 372 (MH$^+$).

Example 23

2-(1-thiophen-2-yl-ethylamino)-5-[1-quinolin-6-yl-meth-(Z)-ylidene]-thiazol-4-one

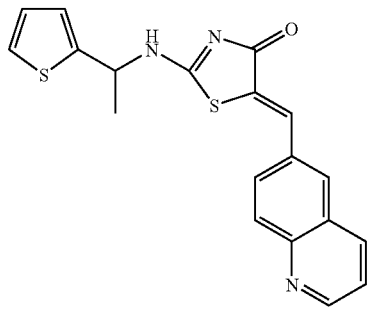

Similar procedure as described in example 1b was used, starting from 2-methylsulfanyl-5-[1-quinolin-6-yl-meth-(Z)-ylidene]-thiazol-4-one, 1-thiophen-2-yl-ethylamine and DIEA to give 2-(1-thiophen-2-yl-ethylamino)-5-[1-quinolin-6-yl-meth-(Z)-ylidene]-thiazol-4-one. LC-MS m/e 366 (MH$^+$).

Example 24

2-(thiazol-2-ylamino)-5-[1-quinolin-6-yl-meth-(Z)-ylidene]-thiazol-4-one

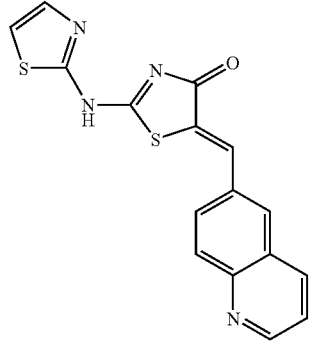

Similar procedure as described in example 1b was used, starting from 2-methylsulfanyl-5-[1-quinolin-6-yl-meth-(Z)-ylidene]-thiazol-4-one, thiazol-2-ylamine and DIEA to give 2-(thiazol-2-ylamino)-5-[1-quinolin-6-yl-meth-(Z)-ylidene]-thiazol-4-one. LC-MS m/e 339 (MH$^+$).

Example 25

2-(2-Hydroxy-1-thiophen-2-yl-ethylamino)-5-[1-quinolin-6-yl-meth-(Z)-ylidene]-thiazol-4-one

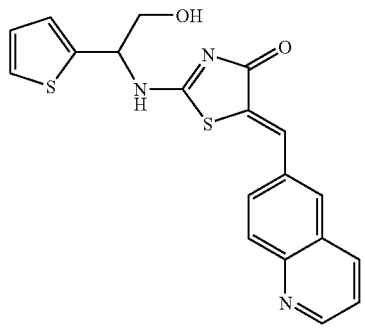

a) Preparation of 2-hydroxy-1-thiophen-2-yl-ethylamine

To the solution of sodium borohydride (1.16 g, 30.5 mmol) in THF (tetrahydrofuran) (25 mL) was added 1-amino-thiophene-2-acetic acid (2.0 g, 12.7 mmol). After cooling to 0° C., the solution of iodine (3.23 g, 12.7 mmol) in THF (25 mL) was added dropwisely. The mixture was stirred at reflux for 18 h. after cooling to the room temperature, methanol (7 mL) was added to stop the reaction. After removal of solvent, 20% potassium hydroxide (50 mL) was added. The mixture was stirred for 4 h and extracted with methylene chloride (3×50 mL). The combined organic layers were dried over sodium sulfate, filtered, and concentrated in vacuo. Flash chromatography (Merck Silica gel 60, 70-230 mesh, 0%-10% methanol in methylene chloride in 30 min afforded 2-hydroxy-1-thiophen-2-yl-ethylamine (1.3 g, 72%).

b) Preparation of 2-(2-hydroxy-1-thiophen-2-yl-ethylamino)-5-[1-quinolin-6-yl-meth-(Z)-ylidene]-thiazol-4-one Then similar procedure as described in example 1b was used, starting from 2-methylsulfanyl-5-[1-quinolin-6-yl-meth-(Z)-ylidene]-thiazol-4-one, 2-hydroxy-1-thiophen-2-yl-ethylamine and DIEA to give 2-(2-hydroxy-1-thiophen-2-yl-ethylamino)-5-[1-quinolin-6-yl-meth-(Z)-ylidene]-thiazol-4-one. LC-MS m/e 382 (MH$^+$).

Example 26

2-[(1,3,5-trimethyl-1H-pyrazol-4-ylmethyl)-amino]-5-[1-quinolin-6-yl-meth-(Z)-ylidene]-thiazol-4-one

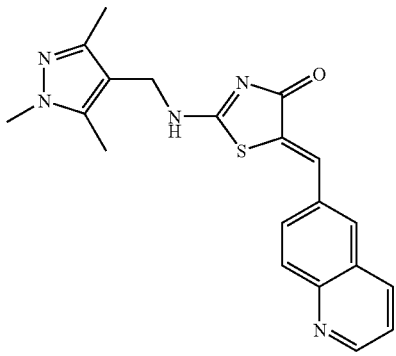

Similar procedure as described in example 1b was used, starting from 2-methylsulfanyl-5-[1-quinolin-6-yl-meth-(Z)-ylidene]-thiazol-4-one, (1,3,5-trimethyl-1H-pyrazol-4-ylmethyl)-amine and DIEA to give 2-[(1,3,5-trimethyl-1H-pyrazol-4-ylmethyl)-amino]-5-[1-quinolin-6-yl-meth-(Z)-ylidene]-thiazol-4-one. LC-MS m/e 378 (MH$^+$).

Example 27

2-((S)-2-Hydroxy-1-phenyl-ethylamino)-5-[1-quinolin-6-yl-meth-(Z)-ylidene]-thiazol-4-one

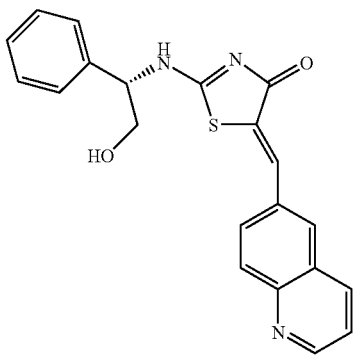

Similar procedure as described in example 1b was used, starting from 2-methylsulfanyl-5-[1-quinolin-6-yl-meth-(Z)-ylidene]-thiazol-4-one, (S)-(+)-phenylglycinol and DIEA to give 2-((S)-2-hydroxy-1-phenyl-ethylamino)-5-[1-quinolin-6-yl-meth-(Z)-ylidene]-thiazol-4-one. LC-MS m/e 376 (MH$^+$).

Example 28

2-((R)-2-Hydroxy-1-phenyl-ethylamino)-5-[1-quinolin-6-yl-meth-(Z)-ylidene]-thiazol-4-one

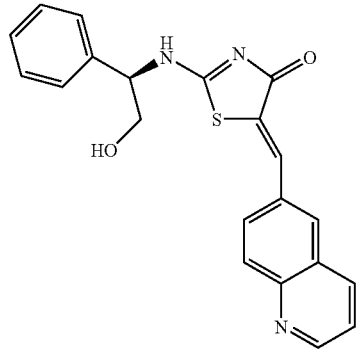

Similar procedure as described in example 1b was used, starting from 2-methylsulfanyl-5-[1-quinolin-6-yl-meth-(Z)-ylidene]-thiazol-4-one, (R)-(−)-phenylglycinol and DIEA to give 2-((R)-2-hydroxy-1-phenyl-ethylamino)-5-[1-quinolin-6-yl-meth-(Z)-ylidene]-thiazol-4-one. LC-MS m/e 376 (MH$^+$).

Example 29

N-(4-Oxo-5-quinolin-6-ylmethylene-4,5-dihydro-thiazol-2-yl)-thiophene-2-carboxamidine

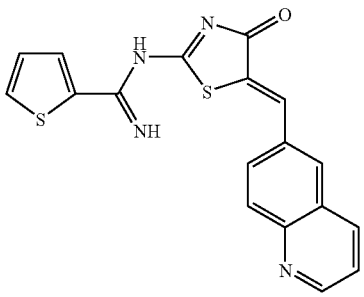

Similar procedure as described in example 1b was used, starting from 2-methylsulfanyl-5-[1-quinolin-6-yl-meth-(Z)-ylidene]-thiazol-4-one, thiophene-2-carboximidamide hydrochloride and DIEA to give N-(4-oxo-5-quinolin-6-ylmethylene-4,5-dihydro-thiazol-2-yl)-thiophene-2-carboxamidine. LC-MS m/e 365 (MH$^+$).

Example 30

2-((1R,2S)-2-Hydroxy-indan-1-ylamino)-5-[1-quinolin-6-yl-meth-(Z)-ylidene]-thiazol-4-one

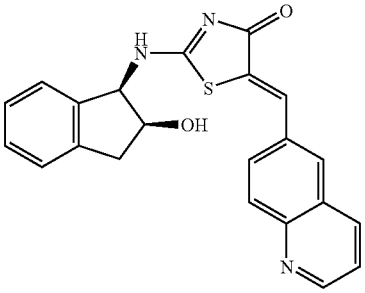

Similar procedure as described in example 1b was used, starting from 2-methylsulfanyl-5-[1-quinolin-6-yl-meth-(Z)-ylidene]-thiazol-4-one, (1R,2S)-(−)-2-hydroxy-indan-1-ylamine and DIEA to give 2-((1R,2S)-2-hydroxy-indan-1-ylamino)-5-[1-quinolin-6-yl-meth-(Z)-ylidene]-thiazol-4-one. LC-MS m/e 388 (MH+).

Example 31

2-[(R)-2-(4-Fluoro-phenyl)-1-hydroxymethyl-ethylamino]-5-[1-quinolin-6-yl-meth-(Z)-ylidene]-thiazol-4-one

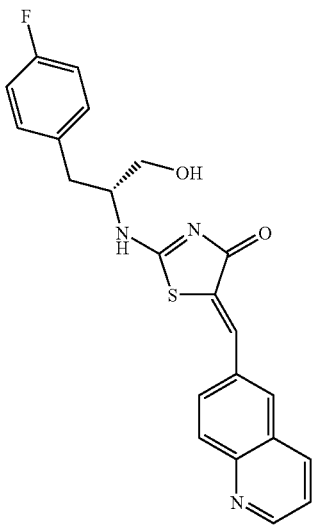

a) Preparation of (R)-2-(4-fluoro-phenyl)-1-hydroxymethyl-ethylamine

To the solution of sodium borohydride (0.48 g, 13.1 mmol) in THF (10 mL) was added D-4-fluorophenylalanine (1.0 g, 5.5 mmol). After cooling to 0° C., the solution of iodine (1.4 g, 5.5 mmol) in THF (10 mL) was added dropwisely. The mixture was stirred at reflux for 18 h. after cooling to the room temperature, methanol (7 mL) was added to stop the reaction. After removal of solvent, 20% potassium hydroxide (50 mL) was added. The mixture was stirred for 4 h and extracted with methylene chloride (3×50 mL). The combined organic layers were dried over sodium sulfate, filtered, and concentrated in vacuo. Flash chromatography (Merck Silica gel 60, 70-230 mesh, 0%-10% methanol in methylene chloride in 30 min afforded (R)-2-(4-fluoro-phenyl)-1-hydroxymethyl-ethylamine (0.73 g, 79%).

b) Preparation of 2-[(R)-2-(4-fluoro-phenyl)-1-hydroxymethyl-ethylamino]-5-[1-quinolin-6-yl-meth-(Z)-ylidene]-thiazol-4-one The similar procedure as described in example 1b was used, starting from 2-methylsulfanyl-5-[1-quinolin-6-yl-meth-(Z)-ylidene]-thiazol-4-one, (R)-2-(4-fluoro-phenyl)-1-hydroxymethyl-ethylamine and DIEA to give 2-[(R)-2-(4-fluoro-phenyl)-1-hydroxymethyl-ethylamino]-5-[1-quinolin-6-yl-meth-(Z)-ylidene]-thiazol-4-one. LC-MS m/e 408 (MH+).

Example 32

2-[(R)-1-(4-Fluoro-phenyl)-2-hydroxy-ethylamino]-5-[1-quinolin-6-yl-meth-(Z)-ylidene]-thiazol-4-one

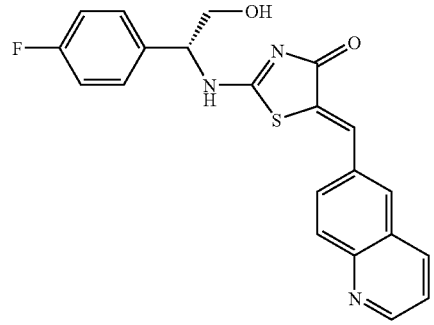

a) Preparation of (R)-2-(4-fluoro-phenyl)-1-hydroxymethyl-ethylamine

To the solution of sodium borohydride (0.54 g, 14.2 mmol) in THF (10 mL) was added D-4-Fluorophenylglycine (1.0 g, 5.9 mmol). After cooling to 0° C., the solution of iodine (1.5 g, 5.9 mmol) in THF (10 mL) was added dropwisely. The mixture was stirred at reflux for 18 h. after cooling to the room temperature, methanol (7 mL) was added to stop the reaction. After removal of solvent, 20% potassium hydroxide (50 mL) was added. The mixture was stirred for 4 h and extracted with methylene chloride (3×50 mL). The combined organic layers were dried over sodium sulfate, filtered, and concentrated in vacuo. Flash chromatography (Merck Silica gel 60, 70-230 mesh, 0%-10% methanol in methylene chloride in 30 min afforded (R)-2-(4-fluoro-phenyl)-1-hydroxymethyl-ethylamine (0.63 g, 69%).

b) Preparation of 2-[(R)-1-(4-fluoro-phenyl)-2-hydroxy-ethylamino]-5-[1-quinolin-6-yl-meth-(Z)-ylidene]-thiazol-4-one Then the similar procedure as described in example 1b was used, starting from 2-methylsulfanyl-5-[1-quinolin-6-yl-meth-(Z)-ylidene]-thiazol-4-one, (R)-4-fluoro-phenylglycinol and DIEA to give 2-[(R)-1-(4-fluoro-phenyl)-2-hydroxy-ethylamino]-5-[1-quinolin-6-yl-meth-(Z)-ylidene]-thiazol-4-one. LC-MS m/e 394 (MH+).

Example 33

2-(3-Hydroxy-2-phenyl-propylamino)-5-[1-quinolin-6-yl-meth-(Z)-ylidene]-thiazol-4-one

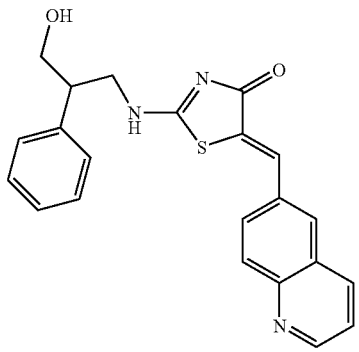

a) Preparation of 3-hydroxy-2-phenyl-propylamine

To the suspension of ethyl phenylcyanoacetate (1.0 g, 5.3 mmol) in anhydrous ether (200 mL) was added lithium aluminum hydride at 0° C. The mixture was stirred at 0° C. for 18 h. After adding water (1 equiv.), 15% sodium hydroxide (1 equiv.) and water (3 equiv.) to the above solution, the precipitation was removed by filtration. The filtrate was concentrate to dry by lyophilization. Flash chromatography (Merck Silica gel 60, 70-230 mesh, 0%-10% methanol in methylene chloride (0.1% NH$_4$OH) in 30 min afforded 3-hydroxy-2-phenyl-propylamine (0.16 g, 20%).

b) Preparation of 2-(3-hydroxy-2-phenyl-propylamino)-5-[1-quinolin-6-yl-meth-(Z)-ylidene]-thiazol-4-one Similar procedure as described in example 1b was used, starting from 2-methylsulfanyl-5-[1-quinolin-6-yl-meth-(Z)-ylidene]-thiazol-4-one, 3-hydroxy-2-phenyl-propylamine and DIEA to give 2-(3-hydroxy-2-phenyl-propylamino)-5-[1-quinolin-6-yl-meth-(Z)-ylidene]-thiazol-4-one. LC-MS m/e 390 (MH$^+$).

Example 34

2-[2-(2-Chloro-phenyl)-2-dimethylamino-ethylamino]-5-[1-quinolin-6-yl-meth-(Z)-ylidene]-thiazol-4-one

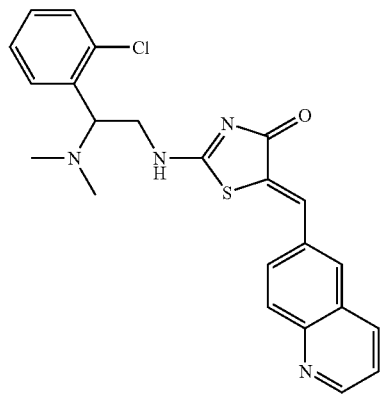

Similar procedure as described in example 1b was used, starting from 2-methylsulfanyl-5-[1-quinolin-6-yl-meth-(Z)-ylidene]-thiazol-4-one, 2-(2-chloro-phenyl)-2-dimethylamino-ethylamine and DIEA to give 2-[2-(2-chloro-phenyl)-2-dimethylamino-ethylamino]-5-[1-quinolin-6-yl-meth-(Z)-ylidene]-thiazol-4-one. LC-MS m/e 438 (MH$^+$).

Example 35

2-(2-Morpholin-4-yl-2-phenyl-ethylamino)-5-[1-quinolin-6-yl-meth-(Z)-ylidene]-thiazol-4-one

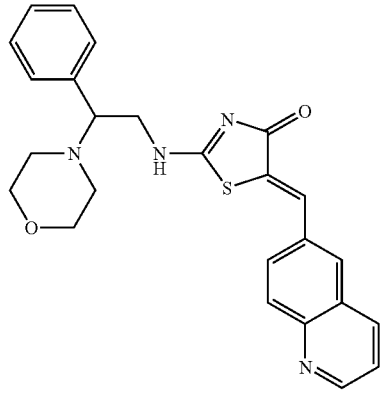

Similar procedure as described in example 1b was used, starting from 2-methylsulfanyl-5-[1-quinolin-6-yl-meth-(Z)-ylidene]-thiazol-4-one, 2-morpholin-4-yl-2-phenyl-ethylamine and DIEA to give 2-(2-morpholin-4-yl-2-phenyl-ethylamino)-5-[1-quinolin-6-yl-meth-(Z)-ylidene]-thiazol-4-one. LC-MS m/e 445 (MH$^+$).

Example 36

2-((R)-1-Hydroxymethyl-propylamino)-5-[1-quinolin-6-yl-meth-(Z)-ylidene]-thiazol-4-one

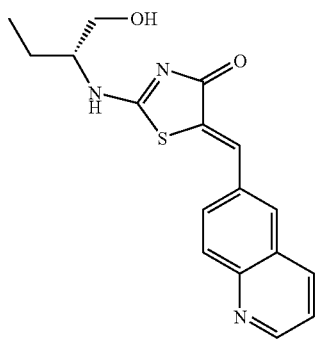

Similar procedure as described in example 1b was used, starting from 2-methylsulfanyl-5-[1-quinolin-6-yl-meth-(Z)-ylidene]-thiazol-4-one, (R)-1-hydroxymethyl-propylamine and DIEA to give 2-((R)-1-hydroxymethyl-propylamino)-5-[1-quinolin-6-yl-meth-(Z)-ylidene]-thiazol-4-one. LC-MS m/e 328 (MH$^+$).

Example 37

2-((R)-1-Hydroxymethyl-2-methyl-propylamino)-5-[1-quinolin-6-yl-meth-(Z)-ylidene]-thiazol-4-one

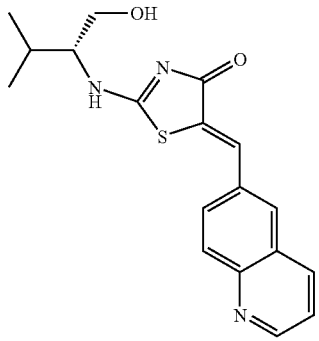

Similar procedure as described in example 1b was used, starting from 2-methylsulfanyl-5-[1-quinolin-6-yl-meth-(Z)-ylidene]-thiazol-4-one, (R)-2-amino-3-methyl-butan-1-ol and DIEA to give 2-((R)-1-hydroxymethyl-2-methyl-propylamino)-5-[1-quinolin-6-yl-meth-(Z)-ylidene]-thiazol-4-one. LC-MS m/e 342 (MH$^+$).

Example 38

2-((R)-1-Hydroxymethyl-3-methyl-butylamino)-5-[1-quinolin-6-yl-meth-(Z)-ylidene]-thiazol-4-one

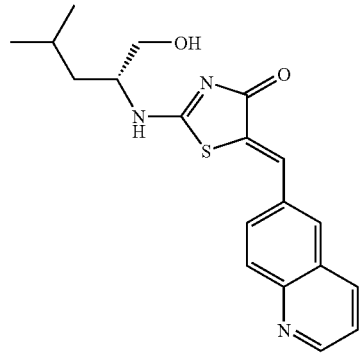

Similar procedure as described in example 1b was used, starting from 2-methylsulfanyl-5-[1-quinolin-6-yl-meth-(Z)-ylidene]-thiazol-4-one, (R)-2-amino-4-methyl-pentan-1-ol and DIEA to give 2-((R)-1-hydroxymethyl-3-methyl-butylamino)-5-[1-quinolin-6-yl-meth-(Z)-ylidene]-thiazol-4-one. LC-MS m/e 356 (MH$^+$).

Example 39

2-[1-(3-Fluoro-phenyl)-2-hydroxy-ethylamino]-5-[1-quinolin-6-yl-meth-(Z)-ylidene]-thiazol-4-one

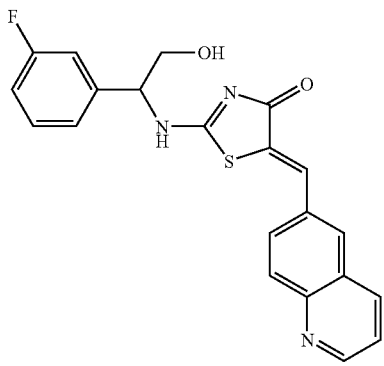

a) Preparation of 3-fluoro-phenylglycinol

Similar procedure as described in example 31a) was used, starting from 3-fluorophenylglycine, sodium borohydride and iodine to give 3-fluoro-Phenylglycinol. LC-MS m/e 156 (MH$^+$).

b) Preparation of 2-[1-(3-fluoro-phenyl)-2-hydroxy-ethylamino]-5-[1-quinolin-6-yl-meth-(Z)-ylidene]-thiazol-4-one Similar procedure as described in example 1b was used, starting from 2-methylsulfanyl-5-[1-quinolin-6-yl-meth-(Z)-ylidene]-thiazol-4-one, 3-fluoro-Phenylglycinol and DIEA to give 2-[1-(3-fluoro-phenyl)-2-hydroxy-ethylamino]-5-[1-quinolin-6-yl-meth-(Z)-ylidene]-thiazol-4-one. LC-MS m/e 394 (MH$^+$).

Example 40

2-[1-(2-Fluoro-phenyl)-2-hydroxy-ethylamino]-5-[1-quinolin-6-yl-meth-(Z)-ylidene]-thiazol-4-one

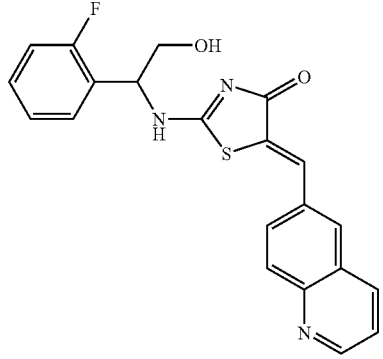

a) Preparation of 2-fluoro-phenylglycinol

Similar procedure as described in example 31a) was used, starting from 2-fluorophenylglycine, sodium borohydride and iodine to give 2-fluoro-Phenylglycinol. LC-MS m/e 156 (MH$^+$).

b) Preparation of 2-[1-(2-fluoro-phenyl)-2-hydroxy-ethylamino]-5-[1-quinolin-6-yl-meth-(Z)-ylidene]-thiazol-4-one Similar procedure as described in example 1b was used, starting from 2-methylsulfanyl-5-[1-quinolin-6-yl-meth-(Z)-ylidene]-thiazol-4-one, 2-fluoro-Phenylglycinol and DIEA to give 2-[1-(2-fluoro-phenyl)-2-hydroxy-ethylamino]-5-[1-quinolin-6-yl-meth-(Z)-ylidene]-thiazol-4-one. LC-MS m/e 394 (MH$^+$).

Example 41

2-(3-Hydroxy-1-phenyl-propylamino)-5-[1-quinolin-6-yl-meth-(Z)-ylidene]-thiazol-4-one

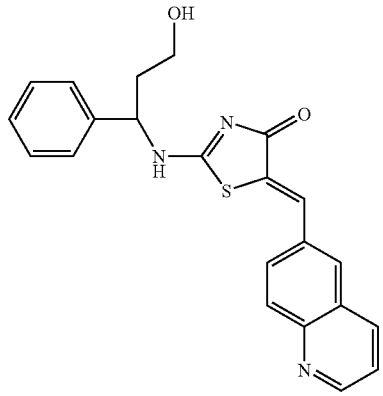

Similar procedure as described in example 1b was used, starting from 2-methylsulfanyl-5-[1-quinolin-6-yl-meth-(Z)-ylidene]-thiazol-4-one, 3-amino-3-phenyl-propan-1-ol and DIEA to give 2-(3-hydroxy-1-phenyl-propylamino)-5-[1-quinolin-6-yl-meth-(Z)-ylidene]-thiazol-4-one. LC-MS m/e 390 (MH$^+$).

Example 42

(R)-2-{4-Oxo-5-[1-quinolin-6-yl-meth-(Z)-ylidene]4,5-dihydro-thiazol-2-ylamino}-2-phenyl-acetamide

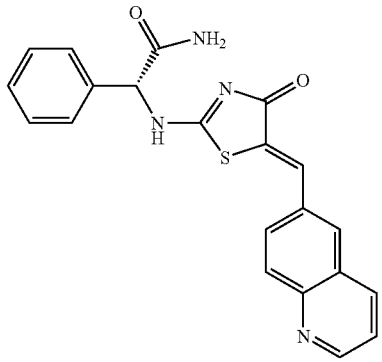

Similar procedure as described in example 1b was used, starting from 2-methylsulfanyl-5-[1-quinolin-6-yl-meth-(Z)-ylidene]-thiazol-4-one, (R)-2-amino-2-phenyl-acetamide hydrochloride and DIEA to give (R)-2-{4-oxo-5-[1-quinolin-6-yl-meth-(Z)-ylidene]-4,5-dihydro-thiazol-2-ylamino}-2-phenyl-acetamide. LC-MS m/e 389 (MH+).

Example 43

2-Methylamino-5-[1-quinolin-6-yl-meth-(Z)-ylidene]-thiazol-4-one

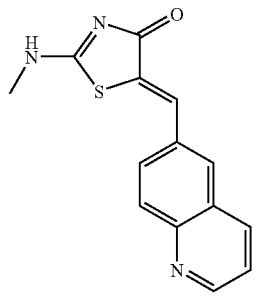

Similar procedure as described in example 1b was used, starting from 2-methylsulfanyl-5-[1-quinolin-6-yl-meth-(Z)-ylidene]-thiazol-4-one, 2N methylamine in THF and DIEA to give 2-methylamino-5-[1-quinolin-6-yl-meth-(Z)-ylidene]-thiazol-4-one. LC-MS m/e 270 (MH+).

Example 44

2-[1-(4-Bromo-phenyl)-2-hydroxy-ethylamino]-5-[1-quinolin-6-yl-meth-(Z)-ylidene]-thiazol-4-one

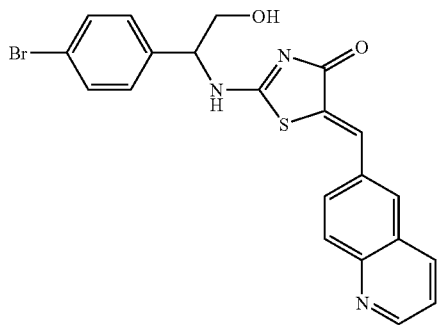

a) Preparation of 4-bromo-phenylglycinol

Similar procedure as described in example 31(a) was used, starting from 4-bromophenylglycine, sodium borohydride and iodine to give 1-(4-bromo-phenyl)-2-hydroxy-ethylamine. LC-MS m/e 216 (MH+).

b) Preparation of 2-[1-(3-fluoro-phenyl)-2-hydroxy-ethylamino]-5-[1-quinolin-6-yl-meth-(Z)-ylidene]-thiazol-4-one Similar procedure as described in example 1b was used, starting from 2-methylsulfanyl-5-[1-quinolin-6-yl-meth-(Z)-ylidene]-thiazol-4-one, 1-(4-bromo-phenyl)-2-hydroxy-ethylamine and DIEA to give 2-[1-(4-bromo-phenyl)-2-hydroxy-ethylamino]-5-[1-quinolin-6-yl-meth-(Z)-ylidene]-thiazol-4-one. LC-MS m/e 455 (MH+).

Example 45

2-[1-(2,4-Difluoro-phenyl)-2-hydroxy-ethylamino]-5-[1-quinolin-6-yl-meth-(Z)-ylidene]-thiazol-4-one

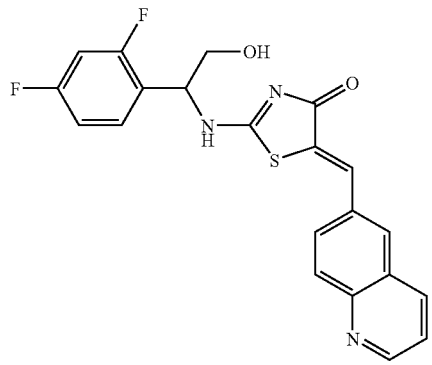

a) Preparation of 1-(2,4-difluoro-phenyl)-2-hydroxy-ethylamine

Similar procedure as described in example 31a) was used, starting from 2,4-diflurophenylglycine, sodium borohydride and iodine to give 1-(2,4-difluoro-phenyl)-2-hydroxy-ethylamine. LC-MS m/e 174 (MH+).

b) Preparation of 2-[1-(2,4-difluoro-phenyl)-2-hydroxy-ethylamino]-5-[1-quinolin-6-yl-meth-(Z)-ylidene]-thiazol-4-one Similar procedure as described in example 1b was used, starting from 2-methylsulfanyl-5-[1-quinolin-6-yl-meth-(Z)-ylidene]-thiazol-4-one, 1-(2,4-difluoro-phenyl)-2-hydroxy-ethylamine and DIEA to give 2-[1-(2,4-difluoro-phenyl)-2-hydroxy-ethylamino]-5-[1-quinolin-6-yl-meth-(Z)-ylidene]-thiazol-4-one. LC-MS m/e 455 (MH+).

Example 46

2-[1-(4-Chloro-phenyl)-2-hydroxy-ethylamino]-5-[1-quinolin-6-yl-meth-(Z)-ylidene]-thiazol-4-one

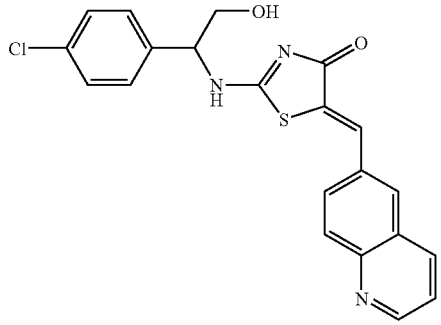

a) Preparation of 1-(4-chloro-phenyl)-2-hydroxy-ethylamine

Similar procedure as described in example 31a was used, starting from 4-chlorophenylglycine, sodium borohydride and iodine to give 1-(4-chloro-phenyl)-2-hydroxy-ethylamine. LC-MS m/e 172 (MH$^+$).

b) Preparation of 2-[1-(3-fluoro-phenyl)-2-hydroxy-ethylamino]-5-[1-quinolin-6-yl-meth-(Z)-ylidene]-thiazol-4-one Similar procedure as described in example 1b was used, starting from 2-methylsulfanyl-5-[1-quinolin-6-yl-meth-(Z)-ylidene]-thiazol-4-one, 1-(4-chloro-phenyl)-2-hydroxy-ethylamine and DIEA to give 2-[1-(4-chloro-phenyl)-2-hydroxy-ethylamino]-5-[1-quinolin-6-yl-meth-(Z)-ylidene]-thiazol-4-one. LC-MS m/e 455 (MH$^+$).

Example 47

(R)-{4-Oxo-5-[1-quinolin-6-yl-meth-(Z)-ylidene]-4,5-dihydro-thiazol-2-ylamino}-phenyl-acetic acid

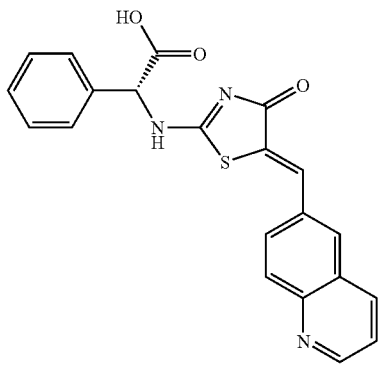

Similar procedure as described in example 1b was used, starting from 2-methylsulfanyl-5-[1-quinolin-6-yl-meth-(Z)-ylidene]-thiazol-4-one, D-phenylglycine and DIEA to give (R)-{4-oxo-5-[1-quinolin-6-yl-meth-(Z)-ylidene]-4,5-dihydro-thiazol-2-ylamino}-phenyl-acetic acid. LC-MS m/e 390 (MH$^+$).

Example 48

2-(2-Hydroxy-ethylamino)-5-[1-quinolin-6-yl-meth-(Z)-ylidene]-thiazol-4-one

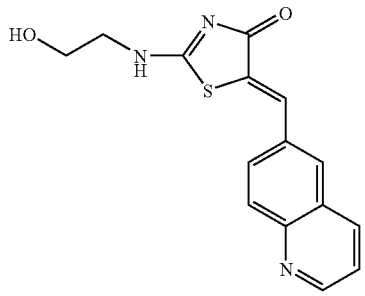

Similar procedure as described in example 1b was used, starting from 2-methylsulfanyl-5-[1-quinolin-6-yl-meth-(Z)-ylidene]-thiazol-4-one, 2-hydroxy-ethylamine and DIEA to give 2-(2-hydroxy-ethylamino)-5-[1-quinolin-6-yl-meth-(Z)-ylidene]-thiazol-4-one. LC-MS m/e 300 (MH$^+$).

Example 49

2-(2-Hydroxy-propylamino)-5-[1-quinolin-6-yl-meth-(Z)-ylidene]-thiazol-4-one

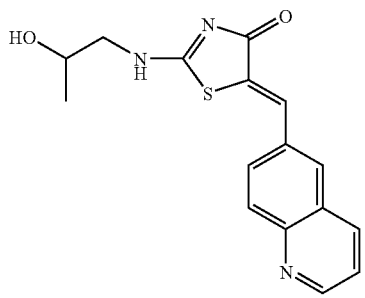

Similar procedure as described in example 1b was used, starting from 2-methylsulfanyl-5-[1-quinolin-6-yl-meth-(Z)-ylidene]-thiazol-4-one, 2-hydroxy-propylamine and DIEA to give 2-(2-hydroxy-propylamino)-5-[1-quinolin-6-yl-meth-(Z)-ylidene]-thiazol-4-one. LC-MS m/e 314 (MH$^+$).

Example 50

2-(2-Hydroxy-2-methyl-propylamino)-5-[1-quinolin-6-yl-meth-(Z)-ylidene]-thiazol-4-one

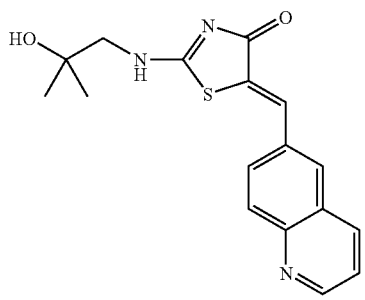

a) Preparation of 2-hydroxy-2-methyl-propylamine

To the solution of acetone cyanohydrin (1 g, 11.7 mmol) and concentrated hydrochloric acid (2 mL) in methanol (40 mL) was added 10% Pd/C (0.2 g). The reaction was carried out under 50 psi of $H_2$ for 12 h. After removal of Pd/C after filtration, the filtrate was concentrated to give crude oil product 2-hydroxy-2-methyl-propylamine which was directly used for next step without further purification.

b) Preparation of 2-(2-hydroxy-2-methyl-propylamino)-5-[1-quinolin-6-yl-meth-(Z)-ylidene]-thiazol-4-one Then similar procedure as described in example 1b was used, starting from 2-methylsulfanyl-5-[1-quinolin-6-yl-meth-(Z)-ylidene]-thiazol-4-one, 2-hydroxy-2-methyl-propylamine and DIEA to give 2-(2-hydroxy-2-methyl-propylamino)-5-[1-quinolin-6-yl-meth-(Z)-ylidene]-thiazol-4-one. LC-MS m/e 328 (MH+).

Example 51

2-(2-Fluoro-6-methoxy-benzylamino)-5-[1-quinolin-6-yl-meth-(Z)-ylidene]-thiazol-4-one

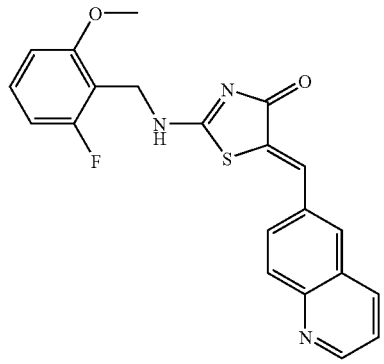

Similar procedure as described in example 1b was used, starting from 2-methylsulfanyl-5-[1-quinolin-6-yl-meth-(Z)-ylidene]-thiazol-4-one, 2-fluoro-6-methoxy-benzylamine and DIEA to give 2-(2-fluoro-6-methoxy-benzylamino)-5-[1-quinolin-6-yl-meth-(Z)-ylidene]-thiazol-4-one. LC-MS m/e 394 (MH+).

Example 52

2-((R)-1-Cyclohexyl-2-hydroxy-ethylamino)-5-[1-quinolin-6-yl-meth-(Z)-ylidene]-thiazol-4-one

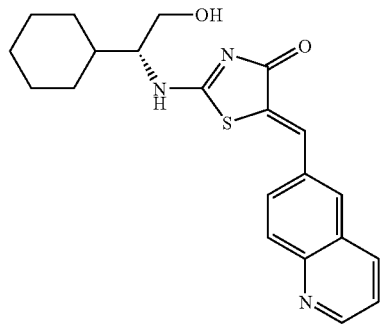

a) Preparation of (R)-1-cyclohexyl-2-hydroxy-ethylamine

Similar procedure as described in example 31a) was used, starting from D-cyclohexylglycine hydrochloride, sodium borohydride and iodine to give (R)-1-cyclohexyl-2-hydroxy-ethylamine. LC-MS m/e 144 (MH+).

b) 2-((R)-1-cyclohexyl-2-hydroxy-ethylamino)-5-[1-quinolin-6-yl-meth-(Z)-ylidene]-thiazol-4-one Similar procedure as described in example 1b was used, starting from 2-methylsulfanyl-5-[1-quinolin-6-yl-meth-(Z)-ylidene]-thiazol-4-one, (R)-1-cyclohexyl-2-hydroxy-ethylamine and DIEA to give 2-((R)-1-cyclohexyl-2-hydroxy-ethylamino)-5-[1-quinolin-6-yl-meth-(Z)-ylidene]-thiazol-4-one. LC-MS m/e 382 (MH+).

Example 53

2-Isobutylamino-5-[1-quinolin-6-yl-meth-(Z)-ylidene]-thiazol-4-one

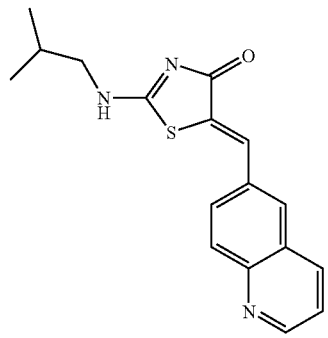

Similar procedure as described in example 1b was used, starting from 2-methylsulfanyl-5-[1-quinolin-6-yl-meth-(Z)-ylidene]-thiazol-4-one, isobutylamine and DIEA to give 2-isobutylamino-5-[1-quinolin-6-yl-meth-(Z)-ylidene]-thiazol-4-one. LC-MS m/e 415 (MH+).

Example 54

2-((1R,2R)-2-Hydroxy-cyclopentylamino)-5-[1-quinolin-6-yl-meth-(Z)-ylidene]-thiazol-4-one

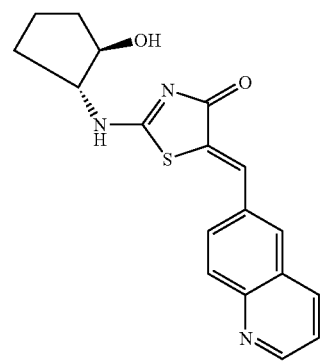

Similar procedure as described in example 1b was used, starting from 2-methylsulfanyl-5-[1-quinolin-6-yl-meth-(Z)-ylidene]-thiazol-4-one, (1R,2R)-2-hydroxy-cyclopentylamine and DIEA to give 2-((1R,2R)-2-hydroxy-cyclopentylamino)-5-[1-quinolin-6-yl-meth-(Z)-ylidene]-thiazol-4-one. LC-MS m/e 340 (MH+).

Example 55

2-((1R,2R)-2-Hydroxy-cyclohexylamino)-5-[1-quinolin-6-yl-meth-(Z)-ylidene]-thiazol-4-one

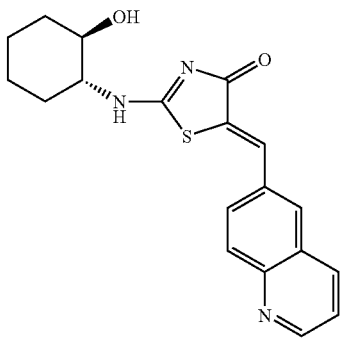

Similar procedure as described in example 1b was used, starting from 2-methylsulfanyl-5-[1-quinolin-6-yl-meth-(Z)-ylidene]-thiazol-4-one, (1R,2R)-2-hydroxy-cyclohexylamine and DIEA to give 2-((1R,2R)-2-hydroxy-cyclohexylamino)-5-[1-quinolin-6-yl-meth-(Z)-ylidene]-thiazol-4-one. LC-MS m/e 354 (MH$^+$).

Example 56

2-((1R,2S)-2-Hydroxymethyl-cyclopropylamino)-5-[1-quinolin-6-yl-meth-(Z)-ylidene]-thiazol-4-one

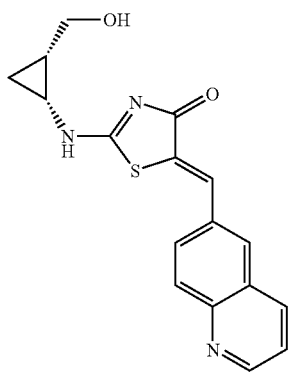

Similar procedure as described in example 1b was used, starting from 2-methylsulfanyl-5-[1-quinolin-6-yl-meth-(Z)-ylidene]-thiazol-4-one, -((1R,2S)-2-hydroxymethyl-cyclopropylamine and DIEA to give 2-((1R,2S)-2-hydroxymethyl-cyclopropylamino)-5-[1-quinolin-6-yl-meth-(Z)-ylidene]-thiazol-4-one. LC-MS m/e 326 (MH$^+$).

Example 57

2-((1R,2R)-2-Hydroxymethyl-cyclopropylamino)-5-[1-quinolin-6-yl-meth-(Z)-ylidene]-thiazol-4-one

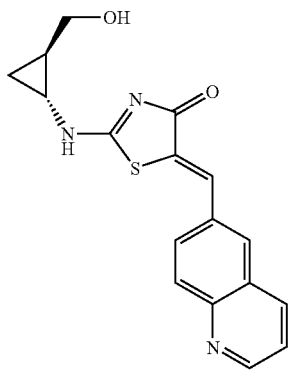

Similar procedure as described in example 1b was used, starting from 2-methylsulfanyl-5-[1-quinolin-6-yl-meth-(Z)-ylidene]-thiazol-4-one, -((1R,2R)-2-hydroxymethyl-cyclopropylamine and DIEA to give 2-((1R,2R)-2-hydroxymethyl-cyclopropylamino)-5-[1-quinolin-6-yl-meth-(Z)-ylidene]-thiazol-4-one. LC-MS m/e 326 (MH$^+$).

Example 58

2-Methoxyamino-5-[1-quinolin-6-yl-meth-(Z)-ylidene]-thiazol-4-one

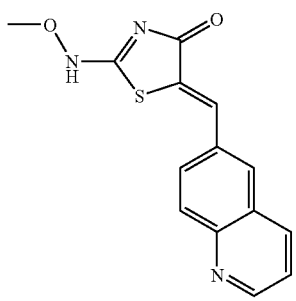

Similar procedure as described in example 1b was used, starting from 2-methylsulfanyl-5-[1-quinolin-6-yl-meth-(Z)-ylidene]-thiazol-4-one, methoxyamine and DIEA to give 2-methoxyamino-5-[1-quinolin-6-yl-meth-(Z)-ylidene]-thiazol-4-one. LC-MS m/e 286 (MH$^+$).

Example 59

2-(2,2-Difluoro-2-pyridin-2-yl-ethylamino)-5-[1-quinolin-6-yl-meth-(Z)-ylidene]-thiazol-4-one hydrochloride

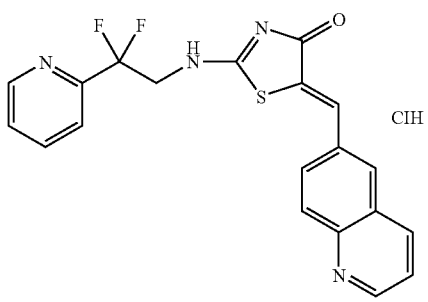

a) Preparation of difluoro-pyridin-2-yl-acetic acid ethyl ester

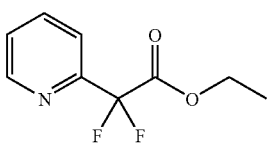

To the solution of 2-bromopyridine (18 mL, 0.2 mmol) and ethyl bromodifluoroacetate (27 g, 0.22 mol) in DMSO (70 mL) was added copper powder (29 g, 0.46 mol). The mixture was stirred at 50° C. for 4 h. After cooling to room temperature, the reaction mixture was diluted with isopropyl acetate (100 mL). A solution of potassium dihydrogen phosphate (1.27 M, 150 mL) was added and stirred for 30 min. the copper salt was removed by filtration and washed with isopropyl acetate (100 mL). The filtrate layer was separated. The organic layer was washed with water (2×100 mL) and dried over sodium sulfate, filtered, and concentrated in vacuo. Flash chromatography (Merck Silica gel 60, 70-230 mesh, 5%-40% methyl t-butyl ether in hexanes in 40 min) afforded difluoro-pyridin-2-yl-acetic acid ethyl ester (27 g, 68%) as a colorless oil. LC-MS m/e 202 (MH$^+$).

b) Preparation of 2,2-difluoro-2-pyridin-2-yl-ethanol

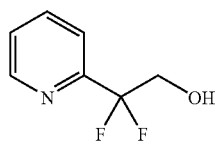

To the solution of difluoro-pyridin-2-yl-acetic acid ethyl ester (example 59a, 10 g, 50 mmol) in ethanol (100 mL) was added sodium borohydride (2 g, 52.5 mmol) in 5 portions at 0° C. After stirring at 0° C. for 1 h and room temperature for 1.5 h, the reaction was quenched by slow addition of hydrochloric acid (2 N) at 0° C. The pH was adjusted to 8.5 with 4N NaOH. The product was extracted with ethyl acetate. The combined organic layers were dried over sodium sulfate, filtered, and concentrated in vacuo. The product was crystallized with heptane afforded 2,2-difluoro-2-pyridin-2-yl-ethanol (6.7 g, 84%) as a white solid.

c) Preparation of 2-(2-azido-1,1-difluoro-ethyl)-pyridine

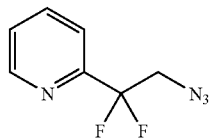

To the solution of 2,2-difluoro-2-pyridin-2-yl-ethanol (example 59b, 5 g, 31.4 mmol) and 2,6-di-t-butyl-4-methylpyridine (9.6 g, 47.1 mmol) in methylene chloride (100 mL) was added dropwisely triflic anhydride (7.9 mL, 47.1 mmol) in methylene chloride (10 mL) at −78° C. under $N_2$. After 1 h, the reaction was warmed to room temperature and continued to stir for 30 min. After adding pentane (100 mL), the solid was removed by filtration. The filtrate was concentrated to give the crude product which was directly used in the next step with further purification.

To the solution of the above crude product in DMF (N,N-dimethylformamide) (70 mL) was added sodium azide (8.2 g, 126 mmol). The reaction was stirred at 60° C. for 12 h. after cooling to room temperature, the solid was removed by filtration and washed with ether. The filtrate was poured into water (300 mL) and extracted with ether (3×300 mL). The combined organic extracts were washed with brine solution and dried over sodium sulfate, filtered, and concentrated in vacuo. Flash chromatography (Merck Silica gel 60, 70-230 mesh, 5%-20% ethyl acetate in hexane in 30 min) afforded 2-(2-azido-1,1-difluoro-ethyl)-pyridine (3.9 g, 67% in 2 steps) as a light yellow oil. LC-MS m/e 185 (MH$^+$).

d) Preparation of 2,2-difluoro-2-pyridin-2-yl-ethylamine

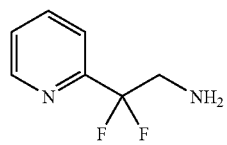

To the solution of 2-(2-azido-1,1-difluoro-ethyl)-pyridine (example 59c, 1 g, 5.4 mmol) in ethyl acetate (50 mL) was added 10% palladium on carbon (0.5 g). The reaction was carried out under $H_2$ in a balloon at room temperature for 2 h. after removal of catalyst, the solvent was concentrated to afford 2,2-difluoro-2-pyridin-2-yl-ethylamine (0.84 g, 98%) as a light yellow oil. LC-MS m/e 158 (MH$^+$).

e) Preparation of 2-(2,2-difluoro-2-pyridin-2-yl-ethylamino)-5-[1-quinolin-6-yl-meth-(Z)-ylidene]-thiazol-4-one hydrochloride Similar procedure as described in example 1b was used, starting from 2-methylsulfanyl-5-[1-quinolin-6-yl-meth-(Z)-ylidene]-thiazol-4-one, 2,2-difluoro-2-pyridin-2-yl-ethylamine (example 59d) and DIEA to give 2-(2,2-difluoro-2-pyridin-2-yl-ethylamino)-5-[1-quinolin-6-yl-meth-(Z)-ylidene]-thiazol-4-one. The product was dissolved in methanol (5 mL). 2 M HCl in ether (2 mL) was added. After adding ether, the solid was collected by filtration, washed with ether and dried to give 2-(2,2-difluoro-2-pyridin-2-yl-ethylamino)-5-[1-quinolin-6-yl-meth-(Z)-ylidene]-thiazol-4-one hydrochloride. LC-MS m/e 397 (MH$^+$).

Example 60

2-[2,2-Difluoro-2-(1-oxy-pyridin-2-yl)-ethylamino]-5-[1-quinolin-6-yl-meth-(Z)-ylidene]-thiazol-4-one

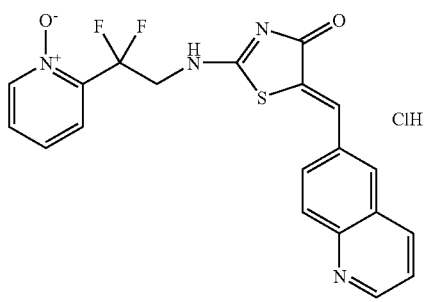

a) Preparation of 2-(2-azido-1,1-difluoro-ethyl)-pyridine N-oxide

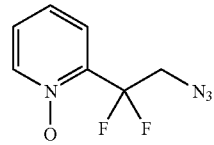

To the solution of 2-(2-azido-1,1-difluoro-ethyl)-pyridine (example 59c, 2.6 g, 14 mmol) and 3-tert-butyl-4-hydroxy-5-methylphenyl sulfide (0.5 g, 1.4 mmol) in 1,2-dichloroethane (40 mL) was added MCPBA (77%, 4.2 g, 18.2 mmol). The reaction mixture was stirred at 55° C. for 12 h. After cooling to room temperature, the reaction mixture was poured into a saturated aqueous $NaHCO_3/NaS_2O_3$ solution (100 mL) and extracted with methylene chloride (3×100 mL). The combined organic extracts were dried over sodium sulfate, filtered, and concentrated in vacuo. Flash chromatography (Merck Silica gel 60, 70-230 mesh, 50%-100% ethyl acetate in hexane in 30 min) afforded 2-(2-azido-1,1-difluoro-ethyl)-pyridine N-oxide (2.7 g, 96%) as a clear oil. LC-MS m/e 201 (MH$^+$).

b) Preparation of 2,2-difluoro-2-pyridin-2-yl-ethylamine N-oxide

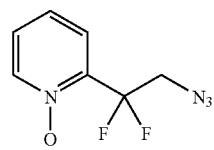

To the solution of 2-(2-azido-1,1-difluoro-ethyl)-pyridine N-oxide (example 60a, 2.7 g, 13.5 mmol) in THF (40 mL)

was slowly added triphenylphosphine (3.9 g, 14.9 mmol) at 0° C. After stirred for 1 h, water (5 mL) was added. The reaction mixture was stirred at 55° C. for 2 h and at room temperature for 12 h. After removal of solvent, the crude was puried by flash chromatography (Merck Silica gel 60, 70-230 mesh, 0%-20% methanol in methylene chloride in 30 min) to give 2,2-difluoro-2-pyridin-2-yl-ethylamine N-oxide (2.2 g, 96%) as a white solid. LC-MS m/e 175 (MH$^+$).

c) Preparation of 2-[2,2-difluoro-2-(1-oxy-pyridin-2-yl)-ethylamino]-5-[1-quinolin-6-yl-meth-(Z)-ylidene]-thiazol-4-one Similar procedure as described in example 59e was used, starting from 2-methylsulfanyl-5-[1-quinolin-6-yl-meth-(Z)-ylidene]-thiazol-4-one, 2,2-difluoro-2-(1-oxy-pyridin-2-yl)-ethylamine and DIEA to give 2-[2,2-difluoro-2-(1-oxy-pyridin-2-yl)-ethylamino]-5-[1-quinolin-6-yl-meth-(Z)-ylidene]-thiazol-4-one. LC-MS m/e 413 (MH$^+$).

Example 61

2-[(Pyridin-2-ylmethyl)-amino]-5-[1-quinolin-6-yl-meth-(Z)-ylidene]-thiazol-4-one

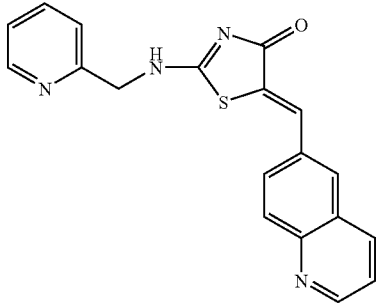

Similar procedure as described in example 1b was used, starting from 2-methylsulfanyl-5-[1-quinolin-6-yl-meth-(Z)-ylidene]-thiazol-4-one, (pyridin-2-ylmethyl)-amine and DIEA to give 2-[(pyridin-2-ylmethyl)-amino]-5-[1-quinolin-6-yl-meth-(Z)-ylidene]-thiazol-4-one. LC-MS m/e 347 (MH$^+$).

Example 62

2-[(S)-1-(3-Methoxy-phenyl)-ethylamino]-5-[1-quinolin-6-yl-meth-(Z)-ylidene]-thiazol-4-one

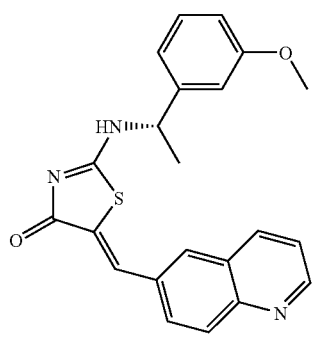

Similar procedure as described in example 1b was used, starting from 2-methylsulfanyl-5-[1-quinolin-6-yl-meth-(Z)-ylidene]-thiazol-4-one, 1-(S)-(3-methoxy-phenyl)-ethylamine and DIEA to give 2-[(S)-1-(3-methoxy-phenyl)-ethylamino]-5-[1-quinolin-6-yl-meth-(Z)-ylidene]-thiazol-4-one. LC-MS m/e 390 (MH$^+$).

Example 63

2-[(S)-1-(4-Methoxy-phenyl)-ethylamino]-5-[1-quinolin-6-yl-meth-(Z)-ylidene]-thiazol-4-one

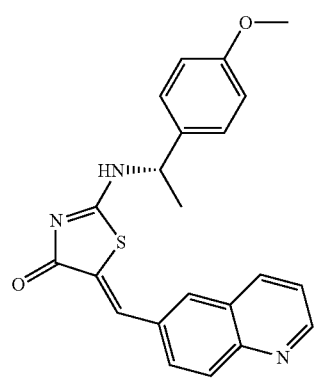

Similar procedure as described in example 1b was used, starting from 2-methylsulfanyl-5-[1-quinolin-6-yl-meth-(Z)-ylidene]-thiazol-4-one, 1-(S)-(4-methoxy-phenyl)-ethylamine and DIEA to give 2-[(S)-1-(4-methoxy-phenyl)-ethylamino]-5-[1-quinolin-6-yl-meth-(Z)-ylidene]-thiazol-4-one. LC-MS m/e 390 (MH$^+$).

Example 64

2-[1-(4-Methanesulfonyl-phenyl)-ethylamino]-5-[1-quinolin-6-yl-meth-(Z)-ylidene]-thiazol-4-one

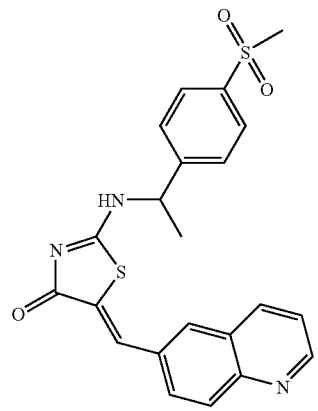

Similar procedure as described in example 1b was used, starting from 2-methylsulfanyl-5-[1-quinolin-6-yl-meth-(Z)-ylidene]-thiazol-4-one, 1-(4-methanesulfonyl-phenyl)-ethylamine and DIEA to give 2-[1-(4-methanesulfonyl-phenyl)-ethylamino]-5-[1-quinolin-6-yl-meth-(Z)-ylidene]-thiazol-4-one. LC-MS m/e 438 (MH$^+$).

Example 65

2-(2-Morpholin-4-yl-ethylamino)-5-[1-quinolin-6-yl-meth-(Z)-ylidene]-thiazol-4-one

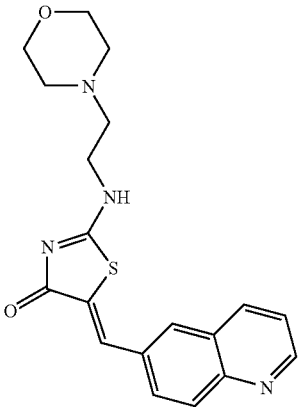

Similar procedure as described in example 1b was used, starting from 2-methylsulfanyl-5-[1-quinolin-6-yl-meth-(Z)-ylidene]-thiazol-4-one, 2-morpholin-4-yl-ethylamine and DIEA to give 2-(2-morpholin-4-yl-ethylamino)-5-[1-quinolin-6-yl-meth-(Z)-ylidene]-thiazol-4-one. LC-MS m/e 368 (MH$^+$).

Example 66

2-(Cyclohexylmethyl-amino)-5-[1-quinolin-6-yl-meth-(Z)-ylidene]-thiazol-4-one

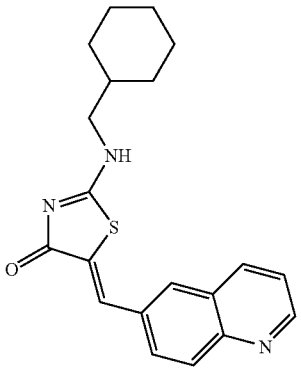

Similar procedure as described in example 1b was used, starting from 2-methylsulfanyl-5-[1-quinolin-6-yl-meth-(Z)-ylidene]-thiazol-4-one, 2-cyclohexyl-methylamine and DIEA to give 2-(cyclohexylmethyl-amino)-5-[1-quinolin-6-yl-meth-(Z)-ylidene]-thiazol-4-one. LC-MS m/e 352 (MH$^+$).

Example 67

2-[(3-methyl-thiophen-2-ylmethyl)-amino]-5-quinolin-6-yl-meth-(Z)-ylidene-thiazol-4-one

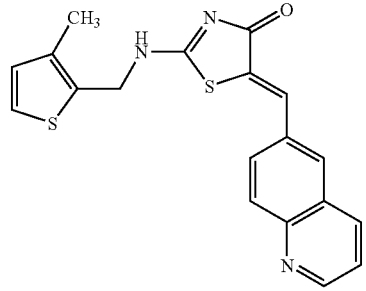

a) Preparation of 2-[(3-methyl-thiophen-2-ylmethyl)-amino]-thiazol-4-one

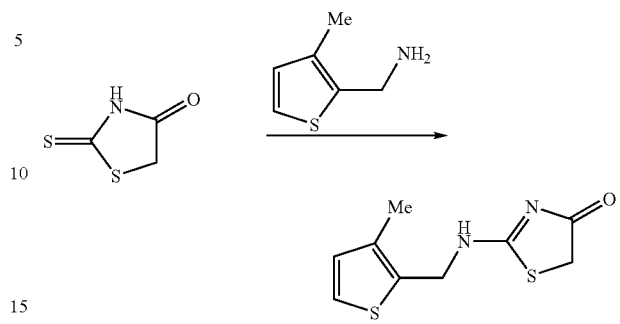

To a solution of 3-methyl-thiophen-2-ylmethylamine (700 mg, 5.5 mmol) and Rhodanine (732 mg, 5.5 mmol) in acetonitrile (30 mL) was added DIPEA (1.91 mL, 11 mmol) at room temperature. Then, this solution was cooled to 0° C. and mercuric chloride (1.52 g, 5.6 mmol) was added in one portion. After addition, the suspension was allowed to warm to room temperature and stirred for 3 days. The resulting black solids were filtered through a plug of celite and washed with acetonitrile (200 mL) and ethyl acetate (250 mL). The filtrates were removed under the vacuum and the crude residue was dissolved in dichloromethane (150 mL) and washed with water and brine solution. After drying over magnesium sulfate, the filtrate was removed under the vacuum and the residue was dissolved in dichloromethane (10 mL) and diluted with hexanes (10 mL). After overnight storage in the refrigerator, the solids were collected by filtration and washed with dichloromethane. After drying in air, 390 mg (31.5% yield) of 2-[(3-methyl-thiophen-2-ylmethyl)-amino]-thiazol-4-one was isolated as a light yellow amorphous solid: EI-HRMS m/e calcd for $C_9H_{10}N_2OS_2$ (M$^+$) 226.0235, found 226.0232.

b) Preparation of 2-[(3-methyl-thiophen-2-ylmethyl)-amino]-5-quinolin-6-ylmeth-(Z)-ylidine-thiazol-4-one

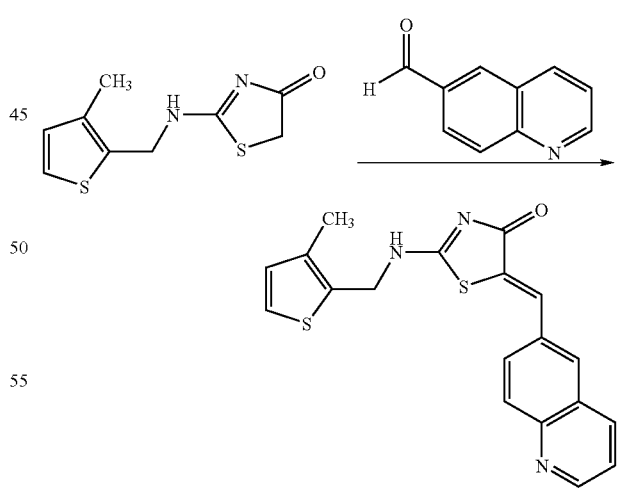

To a suspension of 2-[(3-methyl-thiophen-2-ylmethyl)-amino]-thiazol-4-one (114 mg, 0.5 mmol) and quinoline-6-carbaldehyde (95 mg, 0.6 mmol) in toluene (4 mL) in a microwave tube were added benzoic acid (7.5 mg, 0.06 mmol) and piperidine (6 uL, 0.06 mmol) at room temperature. The microwave tube was sealed and heated to 150° C. in a closed microwave for 30 min. Then, the mixture was cooled to room temperature and diluted with toluene and the mixture was heated with heat gun. After cooling to room temperature, the solids were collected by filtration and washed with toluene and acetonitrile. After drying in air, 84 mg (46% yield) of 2-[(3-methyl-thiophen-2-ylmethyl)-amino]-5-quinolin-6-ylmeth-(Z)-ylidine-thiazol-4-one was isolated as a gray solid. EI-HRMS m/e calcd for $C_{19}H_{15}N_3OS_2$ (M)$^+$, 365.0657, found 365.0652.

Example 68

5-quinolin-6-ylmethylene-2-[(tetrahydro-thiopyran-4-ylmethyl)-amino]-thiazol-4-one

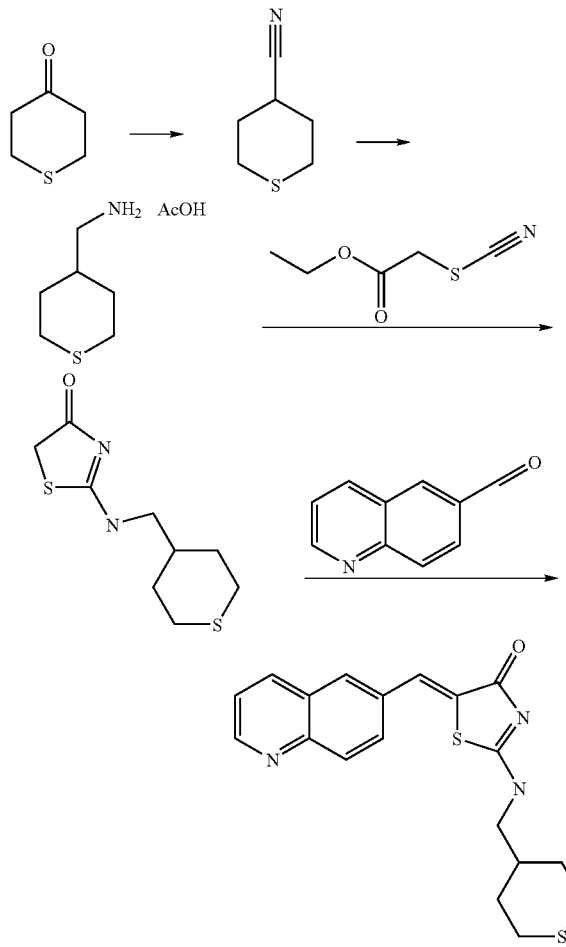

A cold (ice water bath) solution of tetrahydro-4H-thiopyran-4-one (5 g, 43 mmol) and tosylmethylisocyanide (9.24 g, 47.3 mmol) in DME (200 ml) was treated with a suspension of potassium tert-butoxide (9.66 g, 86 mmoles) in tert-butyl alcohol (200 ml). The reaction mixture was stirred at room temperature for 3 hours, and then diluted with ether. The mixture was successively washed with water and brine, then dried over sodium sulfate, filtered, and concentrated. The crude product was purified by short path distillation under high vacuum to give the nitrile as colorless oil (3.06 g). A portion of this material (2 g, 15.7 mmol) was dissolved in 1M borane/THF (80 ml, 80 mmol) and stirred at room temperature for 48 h. Excess borane was quenched by adding methanol (room temperature, 1 h), and the mixture was concentrated to dryness. The residue was dissolved in 4N HCl/dioxane, stirred at room temperature for 1 h and then concentrated under reduced pressure. The solid residue was triturated with ether and collected by suction filtration. A suspension of this material (2.35 g, 14 mmol) in THF (100 ml) was treated with 1N NaOH (14 ml, 14 mmol) at room temperature for ½ h. The THF was removed by distillation and the aqueous solution was saturated with NaCl then extracted with dichloromethane. The organic layer was dried over sodium sulfate and concentrated under reduced pressure. The residue was treated with acetic acid (0.48 ml, 8.5 mmol) to provide, after drying in a vacuum oven, 2-(tetrahydro-thiopyran-4-yl)-methylammonium acetate (1.30 g).

A mixture of 2-(tetrahydro-thiopyran-4-yl)-methylammonium acetate (0.66 g, 3.44 mmol) and thiocyanato-acetic acid ethyl ester (0.50 g, 3.44 mmol) was heated to 90° C. for 2 h. The reaction mixture was partitioned between 6N HCl and dichloromethane. The layers were separated. The aqueous layer was made basic by the addition of 6N ammonium hydroxide, and then extracted with dichloromethane. The organic layer was dried over sodium sulfate and concentrated under reduced pressure. The crude was purified on a silica gel column with 100% ethyl acetate to afford 2-[(tetrahydro-thiopyran-4-ylmethyl)-amino]-thiazol-4-one (299 mg, 38%).

A solution of quinolin-6-carbaldehyde (25 mg, 0.16 mmol) in acetic acid (2 ml) was treated with 2-[(tetrahydro-thiopyran-4-ylmethyl)-amino]-thiazol-4-one (37 mg, 0.16 mmol) and sodium acetate (52.5 mg, 0.64 mmol) in a microwave synthesizer at 180° C. for 1½ h. The reaction mixture was partitioned between 1N NaOH and dichloromethane. The organic layer was dried over sodium sulfate, filtered and concentrated to dryness. The crude was purified by RP HPLC to afford the product as the TFA salt (45 mg). The salt was dissolved in dichloromethane and washed with 1N NaOH. The layers were separated. The organic layer was dried over sodium sulfate and concentrated under reduced pressure to afford the product as the free base (16 mg, 27%). LC-MS m/e 370 (MH$^+$)

Example 69

5-Quinolin-6-ylmethylene-2-[(tetrahydro-pyran-4-ylmethyl)-amino]-thiazol-4-one

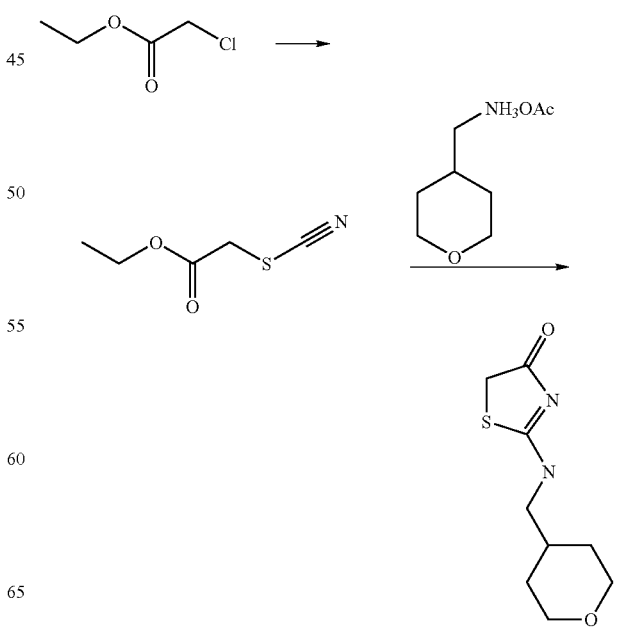

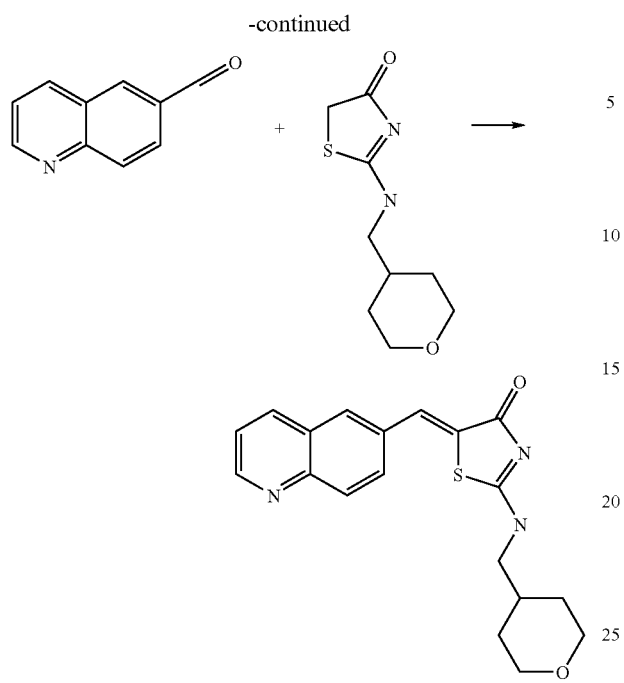

A mixture of 2-(tetrahydropyran-4-yl)-methylammonium acetate (0.54 g, 3.11 mmol) and thiocyanato-acetic acid ethyl ester (0.45 g, 3.11 mmol) was heated to 90° C. for 2 h. The reaction mixture was partitioned between 6N HCl and dichloromethane. The layers were separated. The aqueous layer was made basic by the addition of 6N ammonium hydroxide, and then extracted with dichloromethane. The organic layer was dried over sodium sulfate and concentrated under reduced pressure. The crude was purified on a silica gel column with 100% ethyl acetate to afford 2-[(tetrahydro-pyran-4-ylmethyl)-amino]-thiazol-4-one (118 mg, 18%).

A solution of quinolin-6-carbaldehyde (37 mg, 0.23 mmol) in acetic acid (2 ml) was treated with 2-[(tetrahydro-pyran-4-ylmethyl)-amino]-thiazol-4-one (50 mg, 0.23 mmol) and sodium acetate (76.5 mg, 0.93 mmol) in a microwave synthesizer at 180° C. for 3 h. The reaction mixture was partitioned between 1N NaOH and dichloromethane. The organic layer was dried over sodium sulfate, filtered and concentrated to dryness. The crude was purified by RP HPLC to afford the product as the TFA salt (32 mg, 30%). LC-MS m/e 354 (MH+)

Example 70

2-[(1,1-Dioxo-tetrahydro-thiopyran-4-ylmethyl)-amino]-5-quinolin-6-ylmethylene-thiazol-4-one

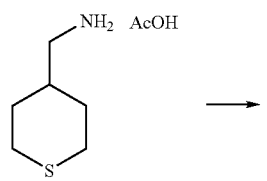

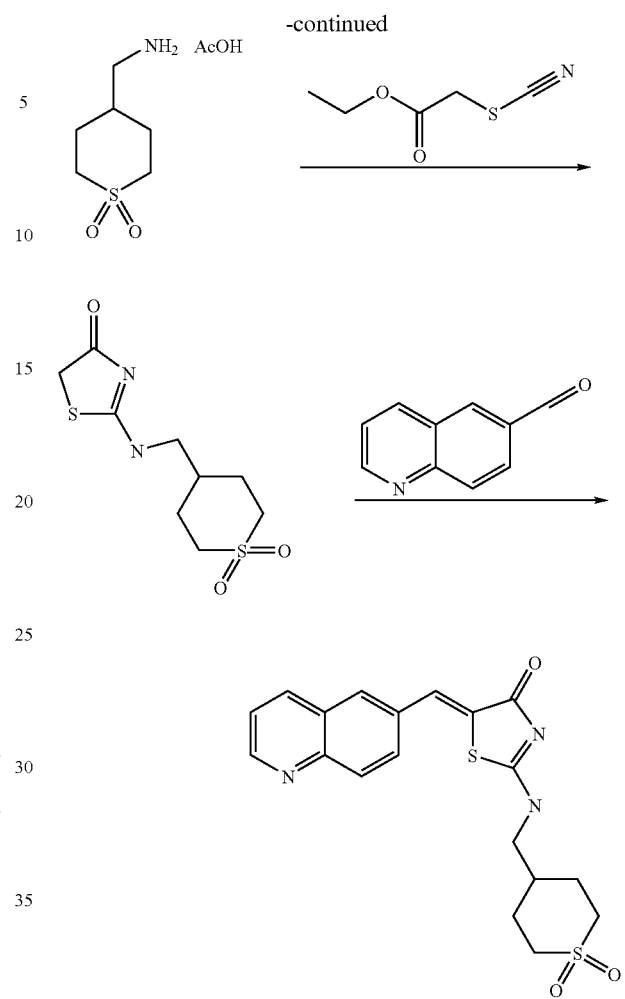

A solution of 2-(tetrahydro-thiopyran-4-yl)-methylammonium acetate (200 mg, 1.05 mmol) in acetic acid (3 ml) was reacted with 30% H$_2$O$_2$ at 60° C. for 4 h. The reaction mixture was concentrated to dryness to afford the desired sulfone (227 mg, 97%).

A mixture of this sulfone (0.23 g, 1.02 mmol) and thiocyanato-acetic acid ethyl ester (0.15 g, 1.02 mmol) was heated to 90° C. for 3 h. The reaction mixture was partitioned between 6N HCl and dichloromethane. The layers were separated. The aqueous layer was made basic by the addition of 6N ammonium hydroxide, and then extracted with dichloromethane. The organic layer was dried over sodium sulfate and concentrated under reduced pressure to afford crude 2-[(1,1-dioxo-tetrahydro-thiopyran-4-yl)-methylamino]-thiazol-4-one (55 mg) which was used in the next step without further purification.

A solution of quinolin-6-carbaldehyde (33 mg, 0.21 mmol) in acetic acid (2 ml) was treated with 2-[(1,1-dioxo-tetrahydro-thiopyran-4-yl)-methylamino]-thiazol-4-one (32 mg, 0.21 mmol) and sodium acetate (69 mg, 0.84 mmol) in a microwave synthesizer at 180° C. for 2 h. The reaction mixture was partitioned between 1N NaOH and dichloromethane. The aqueous layer, which contained the product, was concentrated to dryness. The residue was triturated with DMF. Unsoluble materials were removed by filtration. The DMF solution was concentrated to dryness and the crude was purified by RP HPLC to afford the product as the TFA salt (3 mg, 3%). LC-MS m/e 402 (MH+)

Example 71

2-(Cyclopropylmethyl-amino)-5-quinolin-6-ylmethylene-thiazol-4-one

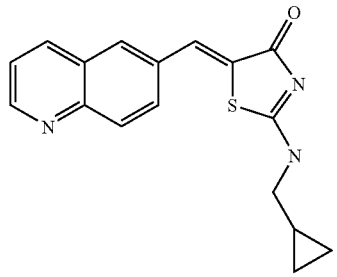

a) Preparation of 2-cyclopropylmethylamino-thiazol-4-one

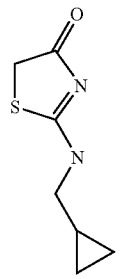

Similar procedure as described in example 67(a) was used, starting from cyclopropylmethylamine, rhodanine (2-thioxo-4-thiazolidinone), mercuric chloride and DIEA to give 2-cyclopropylmethylamino-thiazol-4-one. LC-MS m/e 171 (MH$^+$).

b) Preparation of 2-(cyclopropylmethyl-amino)-5-quinolin-6-ylmethylene-thiazol-4-one A solution of quinolin-6-carbaldehyde (75 mg, 0.48 mmol) in acetic acid (2 ml) was treated with 2-cyclopropylmethylamino-thiazol-4-one (82 mg, 0.48 mmol) and sodium acetate (157 mg, 1.92 mmol) in a microwave synthesizer at 180° C. for 1 h. The reaction mixture was partitioned between 1N NaOH and dichloromethane. The organic layer was dried over sodium sulfate, filtered and concentrated to dryness. The aqueous layer, which contained some product, was concentrated to dryness. The residue was triturated with DMF. Unsoluble materials were removed by filtration. The DMF solution was concentrated to dryness. The combined residues were purified by RP HPLC to afford the product 2-(cyclopropylmethyl-amino)-5-quinolin-6-ylmethylene-thiazol-4-one as the TFA salt (99 mg, 66%). LC-MS m/e 310 (MH$^+$).

Example 72

The pharmacological properties of the compounds of this invention may be confirmed by a number of pharmacological assays. The exemplified pharmacological assays which follow have been carried out with the compounds according to the invention and their salts. The compounds of the invention exhibited CDK1/Cyclin B activity with Ki values of less than 5.0 µM. This demonstrates that all of these compounds were active to inhibit CDK1/Cyclin B.

Kinase Assays

To determine inhibition of CDK1 activity, either FlashPlate™ (NEN™-Life Science Products) assay or HTRF Homogeneous Time Resolved Fluorescence assay was performed. Both types of kinase assays were carried out using recombinant human CDK1/Cyclin B complex. GST-cyclinB (GST-cycB) and CDK1 cDNA clones in baculovirus vectors were provided by Dr. W. Harper at the Baylor College of Medicine, Houston, Tex. Proteins were co-expressed in High Five™ insect cells and the complex was purified on glutathione Sepharose resin (Pharmacia, Piscataway, N.J.) as previously described (Harper, J. W. et al. Cell 1993, 75, 805-816). A 6×-Histidine tagged truncated form of retinoblastoma (Rb) protein (amino acid 386-928) was used as the substrate for the CDK1/Cyclin B assay (the expression plasmid was provided by Dr. Veronica Sullivan, Department of Molecular Virology, Roche Research Centre, Welwyn Garden City, United Kingdom). The Rb protein is a natural substrate for phosphorylation by CDK1 (see Herwig and Strauss Eur. J. Biochem. Vol. 246 (1997) pp. 581-601 and the references cited therein). The expression of the 62Kd protein was under the control of an IPTG inducible promoter in an M15 E. coli strain. Cells were lysed by sonication and purification was carried out by binding lysates at pH 8.0 to a Ni-chelated agarose column pretreated with 1 mM imidazole. The resin was then washed several times with incrementally decreasing pH buffers to pH 6.0, and eluted with 500 mM imidazole. Eluted protein was dialysed against 20 mM HEPES [4-(2-hydroxyethyl)-1-piperazineethanesulfonic acid, sodium salt] pH 7.5, 30% glycerol, 200 mM NaCl, and 1 mM DTT (dithiothreitol). Purified Rb fusion protein stocks were quantitated for protein concentration, aliquoted, and stored at −70° C.

For the FlashPlate kinase asasy, 96-well FlashPlates were coated with Rb protein at 10 µg/ml, using 100 µl per well. Plates were incubated at 4° C. overnight or at room temperature for 3 hours on a shaker. To control for nonspecific phosphorylation, one row of wells was coated with 100 µl/well coating buffer (20 mM HEPES, 0.2 M NaCl). Plates were then washed twice with wash buffer (0.01% Tween 20 in phosphate-buffered saline). Compounds to be tested ("test compounds") were added to the wells at 5× final concentration. Reactions were initiated by immediate addition of 40 µl reaction mix (25 mM HEPES, 20 mM MgCl$_2$, 0.002% Tween 20, 2 mM DTT, 1 µM ATP, 4 nM 33P-ATP) and a sufficient amount of enzyme to give counts that were at least 10-fold above background. Plates were incubated at room temperature on a shaker for 30 minutes. Plates were washed four times with the wash buffer, sealed, and counted on the TopCount scintillation counter (Packard Instrument Co., Downers Grove, Ill.]. The percent inhibition of Rb phosphorylation, which is a measure of the inhibition of CDK activity, was determined according to the following formula:

$$100 \times 1 - \frac{\text{test compound} - \text{nonspecific}}{\text{total} - \text{nonspecific}}$$

where "test compound" refers to the average counts per minute of the test duplicates, "nonspecific" refers to the average counts per minute when no CDK1/Cyclin B, etc., was added, and "total" refers to the average counts per minute when no compound was added. The IC$_{50}$ value is the concentration of test compound that reduces by 50% the protein-kinase induced incorporation of the radiolabel under the test conditions described. The value of the inhibitor constant Ki is calculated by the following: Ki=IC50/(1+[S]/Km), where [S] is the ATP concentration and Km is Michaelis constant.

The Homogeneous Time Resolved Fluorescence (HTRF) kinase assay was carried out in 96-well polypropylene plates (BD Biosciences, Bedford, Mass.). Test compounds were first dissolved in DMSO, and then diluted in kinase assay buffer 1 (25 mM HEPES, pH7.0, 8 mM $MgCl_2$, 1.5 mM DTT, and 162 µM ATP) with DMSO concentration at 15%. The CDK1/Cyclin B enzyme was diluted in kinase assay buffer 2 (25 mM HEPES, pH 7.0, 8 mM $MgCl_2$, 0.003% Tween 20, 0.045% BSA, 1.5 mM DTT, and 0.338 µM Rb protein). To initiate the kinase reaction, 20 µL of compound solution was mixed with 40 µL of CDK1/Cyclin B solution in assay plates with final concentration of CDK1/Cyclin B and Rb at 0.1 µg/mL and 0.113 µM, respectively, and incubated at 37° C. for 30 min. 15 µL of anti-phospho-Rb (Ser 780) antibody (Cell Signaling Technology, Beverly, Mass.) was added with a 1:7692 dilution of the antibody. Incubation was continued at 37° C. for 25 min, after which LANCE Eu-W1024 labeled anti-rabbit IgG (1 nM, PerkinElmer, Wellesley, Mass.) and anti-His antibody conjugated to SureLight-Allophucocyanin (20 nM, PerkinElmer, Wellesley, Mass.) were added to the wells. Incubation was continued at 37° C. for another 40 min. At the completion of the incubation, 35 µL of reaction mixture was transferred to fresh 384-well black polystyrene plates (Corning Incorporated, Corning, N.Y.) and read on a fluorescent plate reader at excitation wavelength of 340 nm and emission wavelength of 665/615 nm.

Ki values showing CDK1/Cyclin B activity that applied to compounds of the subject matter of this invention ranges from about 0.001 µM to about 5.000 µM. Specific data for some examples are as follows:

| Example | Ki (µM) |
|---------|---------|
| 5 | 0.838 |
| 10 | 0.148 |
| 15 | 0.798 |
| 20 | 0.604 |
| 25 | 0.596 |
| 30 | 3.000 |
| 35 | 3.300 |

What is claimed is:

1. A compound of the formula:

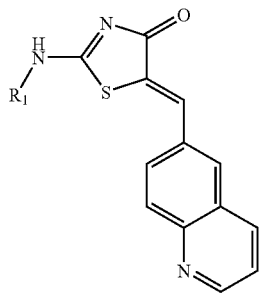

I wherein
  $R_1$ is selected from lower alkyl, lower alkoxy, aryloxy lower alkyl, hydroxyl lower alkyl, lower alkoxy lower alkyl, and $R_2$—$(X)_n$—;
  X is selected from lower alkylene, hydroxy substituted lower alkylene, cyclo lower alkylene, aryl substituted lower alkylene, carboxy substituted lower alkylene, amido substituted lower alkylene, mono- or di-halo substituted lower alkylene, amino substituted lower alkylene, mono- or di-lower alkyl amino substituted lower alkylene and imido substituted lower alkylene;
  $R_2$ is

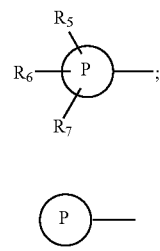

is a carbon containing ring connected by a ring carbon atom, said ring being selected from an aryl ring, cycloalkyl ring containing from 3 to 6 carbon atoms, a 4 to 6 membered heterocycloalkyl ring containing from 3 to 5 carbon atoms and from 1 to 2 hetero atoms selected from oxygen, nitrogen and sulfur, and a 4 to 6 membered heteroaromatic ring containing from 1 to 2 hetero atoms selected from oxygen, sulfur and nitrogen;

$R_5$, $R_6$ and $R_7$ are independently selected from hydroxy, —$SO_2CH_3$, hydroxy-lower alkyl, amino, hydrogen, lower alkyl, halogen, lower alkoxy and mono- or di-lower alkyl amino, or when two of the substituents $R_5$, $R_6$ and $R_7$ are substituted on adjacent carbon atoms on ring Ⓟ, these two substituents can be taken together with their adjacent, attached carbon atoms to form a group selected from an aryl ring, a 3 to 6 membered cycloalkyl ring, a 4 to 6 membered heterocycloalkyl ring or a 4 to 6 membered heteroaromatic ring with said heterocycloalkyl ring and said heteroaromatic ring containing from 1 to 2 hetero atoms selected from oxygen, nitrogen and sulfur, and n is an integer from 0 to 1; with the proviso that when Ⓟ is an aryl ring, then n is 1 and with the further proviso that when Ⓟ is an aryl ring, n is 1 and X is lower alkylene, then one of $R_5$, $R_6$ and $R_7$ is other than hydrogen, halogen, or lower alkyl; and with the still further proviso that when Ⓟ is a cycloalkyl ring and n is 0, then one $R_5$, $R_6$ and $R_7$ is other than hydrogen or lower alkyl; or N-oxides of compounds where $R_2$ contains a nitrogen in the heteroaromatic ring, sulfones where $R_2$ contains a sulfur in the heterocycloalkyl ring; or pharmaceutically acceptable salts thereof.

2. The compound of claim 1 wherein P is a phenyl ring.

3. The compound of claim 1 wherein said compound has the formula:

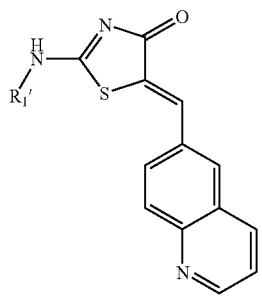

I-A wherein
  $R_1'$ is selected from lower alkyl, lower alkoxy, hydroxy lower alkyl, lower alkoxy lower alkyl and phenoxy lower alkyl;

or pharmaceutically acceptable salts thereof.

4. The compound of claim 3 wherein $R_1'$ is lower alkyl.

5. The compound of claim 4 wherein said compound is 2-pentylamino-5-[1-quinolin-6-yl-meth-(Z)-ylidene]-thiazol-4-one.

6. The compound of claim 4 wherein said compound is 2-methylamino-5-[1-quinolin-6-yl-meth-(Z)-ylidene]-thiazol-4-one.

7. The compound of claim 4 wherein said compound is 2-isobutylamino-5-[1-quinolin-6-yl-meth-(Z)-ylidene]-thiazol-4-one.

8. The compound of claim 2 wherein $R_1'$ is hydroxy lower alkyl or lower alkoxy lower alkyl.

9. The compound of claim 8 wherein said compound is 2-(1-hydroxymethyl-propylamino)-5-[1-quinolin-6-yl-meth-(Z)-ylidene]-thiazol-4-one.

10. The compound of claim 8 wherein said compound is 2-(1-hydroxymethyl-2-methyl-propylamino)-5-[1-quinolin-6-yl-meth-(Z)-ylidene]-thiazol-4-one.

11. The compound of claim 8 wherein said compound is 2-(1-hydroxymethyl-3-methyl-butylamino)-5-[1-quinolin-6-yl-meth-(Z)-ylidene]-thiazol-4-one.

12. The compound of claim 8 wherein said compound is 2-(2-hydroxy-2-methyl-propylamino)-5-[1-quinolin-6-yl-meth-(Z)-ylidene]-thiazol-4-one.

13. The compound of claim 3 wherein $R_1'$ is phenoxy-lower alkyl.

14. The compound of claim 13 wherein said compound is 2-(2-phenoxy-ethylamino)-5-[1-quinolin-6-yl-meth-(Z)-ylidene]-thiazol-4-one.

15. The compound of claim 1 wherein said compound has the formula:

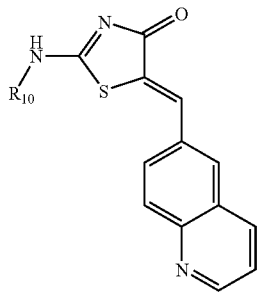

I-B wherein $R_{10}$ is

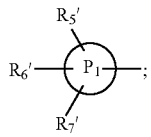

is a cycloalkyl ring containing from 3 to 6 carbon atoms;
  $R_5'$ is selected from hydroxy, —SO$_2$CH$_3$, hydroxy-lower alkyl, amino, halogen, lower alkoxy, mono- or di-lower alkyl amino; and
  $R_6'$ and $R_7'$ are independently selected from hydroxy, SO$_2$CH$_3$, hydroxy-lower alkyl, amino, hydrogen, lower alkyl, halogen, lower alkoxy, and mono- or di-lower alkyl amino, or when two of the substituents $R_5'$, $R_6'$ and $R_7'$ are substituents on adjacent carbon atoms on ring

these two substituents can be taken together with their adjacent, attached carbon atoms to form a group selected from an aryl ring, a 3 to 6 membered cycloalkyl ring, a 4 to 6 membered heterocycloalkyl ring and a 4 to 6 membered heteroaromatic ring containing from 1 to 2 hetero atoms with said heterocycloalkyl ring and said heteroaromatic ring containing from 1 to 2 hetero atoms selected from oxygen, nitrogen, and sulfur; or N-oxides of compounds where $R_{10}$ contains a nitrogen in the heteroaromatic ring, sulfones where $R_{10}$ contains a sulfur in the heterocycloalkyl ring; or pharmaceutically acceptable salts thereof.

16. The compound of claim 15 wherein $R_5'$ is hydroxy or hydroxy lower alkyl and $R_6$ and $R_7$ are hydrogen or lower alkoxy.

17. The compound of claim 16 wherein said compound is 2-hydroxy-cyclopentylamino)-5-[1-quinolin-6-yl-meth-(Z)-ylidene]-thiazol-4-one.

18. The compound of claim 16 wherein said compound is 2-hydroxy-cyclohexylamino)-5-[1-quinolin-6-yl-meth-(Z)-ylidene]-thiazol-4-one.

19. The compound of claim 16 wherein said compound is 2-hydroxymethyl-cyclopropylamino)-5-[1-quinolin-6-yl-meth-(Z)-ylidene]-thiazol-4-one.

20. The compound of claim 15 where both of $R_6'$ and $R_7'$ are substituted on adjacent carbon atoms and taken together with the attached carbon atoms form a phenyl or a heteroaromatic ring.

21. The compound of claim 20 wherein said compound is 2-(2-hydroxy-indan-1-ylamino)-5-[1-quinolin-6-yl-meth-(Z)-ylidene]-thiazol-4-one.

22. The compound of claim 1 wherein said compound has the formula:

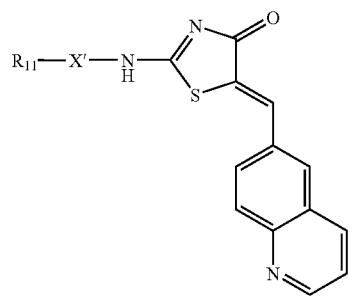

I-C wherein X' is lower alkylene and $R_{11}$ is

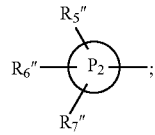

is an aryl ring,
R$_5$" is selected from hydroxy, hydroxy-lower alkyl, amino, lower alkoxy and mono- or di-lower alkyl amino; and
R$_6$" and R$_7$" are selected from hydroxy, hydroxy-lower alkyl, amino, hydrogen, lower alkyl, halogen, lower alkoxy and mono- or di-lower alkyl amino, or when two of the substituents R$_5$" R$_6$" and R$_7$" are substituted on adjacent carbon atoms on ring

, these two substituents can be taken together with their adjacent, attached carbon atoms to form a group selected from an aryl ring, a 3 to 6 membered cycloalkyl ring, a 4 to 6 membered heterocycloalkyl ring and a 4 to 6 membered heteroaromatic ring with said heterocycloalkyl ring and said heteroaromatic ring containing from 1 to 2 hetero atoms selected from oxygen, nitrogen and sulfur, with the proviso that one of R$_5$", R$_6$" and R$_7$" is other than hydrogen, halogen, or lower alkyl; or
N-oxides of compounds where R$_{11}$ contains a nitrogen in the heteroaromatic ring, sulfones where R$_{11}$ contains a sulfur in the heterocycloalkyl ring; or
pharmaceutically acceptable salts thereof.

23. The compound of claim 22 wherein P$_2$ is a phenyl ring.

24. The compound claim 23 wherein R$_5$" is lower alkoxy and R$_6$" and R$_7$" is hydrogen.

25. The compound of claim 24 wherein said compound is 2-[2-(4-methoxy-phenyl)-ethylamino]-5-[1-quinolin-6-yl-meth-(Z)-ylidene]-thiazol-4-one.

26. The compounds claim 24 wherein said compound is 2-[2-(2-ethoxy-phenyl)-ethylamino]-5-[1-quniolin-6-yl-meth-(Z)-ylidene]-thiazol-4-one.

27. The compound of claim 24 where said compound is 2-[2-(2-methoxy-phenyl)-ethylamino]-5-[1-quinolin-6-yl-meth-(Z)-ylidene]-thiazol-4-one.

28. The compound of claim 24 wherein said compound is 2-(2-methoxy-benzylamino)-5-[1-quinolin-6-yl-meth-(Z)-ylidene]-thiazol-4-one.

29. The compound of claim 24 wherein said compound is 2-[2-(2,5-dimethoxy-phenyl)-ethylamino]-5-[1-quinolin-6-yl-meth-(Z)-ylidene]-thiazol-4-one.

30. The compound of claim 24 wherein said compound is 2-[1-(3-methoxy-phenyl)-ethylamino]-5-[1-quinolin-6-yl-meth-(Z)-ylidene]-thiazol-4-one.

31. The compound of claim 24 wherein said compound is 2-[1-(4-methoxy-phenyl)-ethylamino]-5-[1-quinolin-6-yl-meth-(Z)-ylidene]-thiazol-4-one.

32. The compound of claim 23 wherein R$_5$" is lower alkoxy and one of R$_6$" and R$_7$" is halogen.

33. The compound of claim 32 wherein said compound is 2-(2-fluoro-6-methoxy-benzylamino)-5-[1-quinolin-6-yl-meth-(Z)-ylidene]-thiazol-4-one.

34. The compound of claim 23 wherein R$_7$" is amino, lower alkyl amino or di lower alkyl amino.

35. The compound of claim 34 where said compound is 2-[2-(4-amino-phenyl)-ethylamino]-5-[1-quinolin-6-yl-meth-(Z)-ylidene]-thiazol-4-one.

36. The compound of claim 23 wherein R$_6$" and R$_7$" are substituted on adjacent carbon atoms on the phenyl ring and taken together with their adjacent carbon atoms form a lower alkyleneoxy or lower alkylenedioxy bridge to produce a heterocycloalkyl ring.

37. The compound of claim 36 wherein said compound is 2-[(2,3-dihydrobenzofuran-5-ylmethyl)-amino]-5-[1-quinolin-6-yl-meth-(Z)-ylidene]-thiazol-4-one.

38. The compound of claim 36 wherein said compound is 2-(2-benzo[1,3]dioxol-5-yl-ethylamino)-5-[1-quinolin-6-yl-meth-(Z)-ylidene]-thiazol-4-one.

39. The compound of claim 1 wherein said compound has the formula:

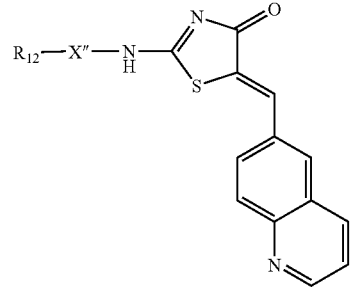

I-D wherein
R$_{12}$ is

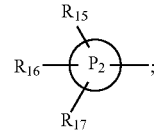;

is an aryl ring;
X" is selected from hydroxy-lower alkylene, cyclo lower alkylene, aryl lower alkylene, mono- or di-halo lower alkylene, amino lower alkylene, mono- or di-lower alkyl amino lower alkylene and imido lower alkylene;
R$_{15}$, R$_{16}$ and R$_{17}$ are independently selected from hydroxy, SO$_2$CH$_3$, hydroxy-lower alkyl, amino, hydrogen, lower alkyl, halogen, lower alkoxy, mono- or di-lower alkyl amino, or when two of the substituents R$_{15}$, R$_{16}$ and R$_{17}$ are substituted on adjacent carbon atoms on ring

, these two substituents can be taken together with their adjacent, attached carbon atoms to form a group selected from an aryl ring, a 3 to 6 membered cycloalkyl ring, a 4 to 6 membered heterocycloalkyl ring and a 4 to 6 membered heteroaromatic ring with said heterocycloalkyl ring and said heteroaromatic ring containing from 1 to 2 hetero atoms selected from oxygen, nitrogen and sulfur, with the proviso that one of $R_{15}$, $R_{16}$ and $R_{17}$ is other than hydrogen, halogen, or lower alkyl; or N-oxides of compounds where $R_{12}$ contains a nitrogen in the heteroaromatic ring, sulfones where $R_{12}$ contains a nitrogen in the heterocycloalkyl ring; or pharmaceutically acceptable salts thereof.

40. The compounds of claim 39 wherein $P_2$ is a phenyl.

41. The compounds of claim 40 wherein X" is hydroxy-loweralkylene.

42. The compound of claim 41 where $R_{15}$, $R_{16}$ and $R_{17}$ are hydrogen.

43. The compound of claim 42 where said compound is 2-(1-hydroxymethyl-2-phenyl-ethylamino)-5-[1-quinolin-6-yl-meth-(Z)-ylidene]-thiazol-4-one.

44. The compound of claim 42 where said compound is 2-(3-hydroxy-1-phenyl-propylamino)-5-[1-quinolin-6-yl-meth-(Z)-ylidene]-thiazol-4-one.

45. The compound of claim 42 wherein said compound is 2-(2-hydroxy-1-phenyl-ethylamino)-5-[1-quinolin-6-yl-meth-(Z)-ylidene]-thiazol-4-one.

46. The compound of claim 42 wherein said compound is 2-(3-Hydroxy-2-phenyl-propylamino)-5-[1-quinolin-6-yl-meth-(Z)-ylidene]-thiazol-4-one.

47. The compound of claim 41 wherein $R_{15}$, $R_{16}$ and $R_{17}$ are hydrogen or halogen where at least one of $R_{15}$, $R_{16}$ and $R_{17}$ is halogen.

48. The compound of claim 47 wherein said compound is 2-[1-(4-chloro-phenyl)-2-hydroxy-ethylamino]-5-[1-quinolin-6-yl-meth-(Z)-ylidene]-thiazol-4-one.

49. The compound of claim 47 wherein said compound is 2-[2-(4-fluoro-phenyl)-1-hydroxymethyl-ethylamino]-5-[1-quinolin-6-yl-meth-(Z)-ylidene]-thiazol-4-one.

50. The compound of claim 47 wherein said compound is 2-[1-(4-fluoro-phenyl)-2-hydroxy-ethylamino]-5-[1-quinolin-6-yl-meth-(Z)-ylidene]-thiazol-4-one.

51. The compound of claim 47 wherein said compound is 2-[1-(3-fluoro-phenyl)-2-hydroxy-ethylamino]-5-[1-quinolin-6-yl-meth-(Z)-ylidene]-thiazol-4-one.

52. The compound of claim 47 wherein said compound is 2-[1-(2-fluoro-phenyl)-2-hydroxy-ethylamino]-5-[1-quinolin-6-yl-meth-(Z)-ylidene]-thiazol-4-one.

53. The compound of claim 40 wherein X" is amido lower alkylene or carboxyloweralkylene.

54. The compound of claim 53 wherein said compound is 2-{4-oxo-5-[1-quinolin-6-yl-meth-(Z)-ylidene]-4,5-dihydro-thiazol-2-ylamino}-2-phenyl-acetamide.

55. The compound of claim 53 wherein said compound is 4-oxo-5-[1-quinolin-6-yl-meth-(Z)-ylidene]-4,5-dihydro-thiazol-2-ylamino}-phenyl-acetic acid.

56. The compound of claim 40 wherein X" is amino lower alkylene, mono- or di-lower alkylamino lower alkylene or imidoloweralkylene.

57. The compound of claim 56 wherein said compound is 2-[2-(2-chloro-phenyl)-2-dimethylamino-ethylamino]-5-[1-quinolin-6-yl-meth-(Z)-ylidene]-thiazol-4-one.

58. The compound of claim 1 wherein said compound has the formula:

I-E wherein X is as above;

$R_{13}$ is is a carbon containing ring attached through its carbon atom, which ring is selected from cycloalkyl ring containing from 2 to 6 carbon atoms, a 4 to 6 membered heterocycloalkyl ring containing from 3 to 5 carbon atoms and from 1 to 2 hetero atoms selected from oxygen, nitrogen and sulfur, and a 4 to 6 membered heteroaromatic ring containing from 1 to 2 hetero atoms selected from oxygen, sulfur, and nitrogen;

$R_{15}$, $R_{16}$ and $R_{17}$ are independently selected from hydroxy, $SO_2CH_3$, hydroxy-lower alkyl, amino, hydrogen, lower alkyl, halogen, lower alkoxy, mono- or di-lower alkyl amino, or when two of the substituents $R_{15}$, $R_{16}$ and $R_{17}$ are substituted on adjacent carbon atoms on ring these two substituents can be taken together with their adjacent, attached carbon atoms to form a group selected from an aryl ring, a 3 to 6 membered cycloalkyl ring, a 4 to 6 membered heterocycloalkyl ring and a 4 to 6 membered heteroaromatic ring with said heterocycloalkyl ring and said heteroaromatic ring containing from 1 to 2 hetero atoms selected from oxygen, nitrogen and sulfur; or N-oxides of compounds where $R_{13}$ contains a nitrogen in the heteroaromatic ring, sulfones where $R_{13}$ contains a sulfur in the heterocycloalkyl ring or;

pharmaceutically acceptable salts thereof.

59. The compound of claim 58 wherein X is lower alkylene.

60. The compound of claim 59 where

is a cycloalkyl ring.

61. The compound of claim 60 wherein $R_{15}$, $R_{16}$ and $R_{17}$ are hydrogen.

62. The compound of claim 61 wherein said compound is 2-(cyclopropylmethylamino)-5-[1-quinolin-6-yl-meth-(Z)-ylidene]-thiazol-4-one.

63. The compound of claim 61 wherein said compound is 2-(cyclohexylmethyl-amino)-5-[1-quinolin-6-yl-meth-(Z)-ylidene]-thiazol-4-one.

64. The compound of claim 59 where

is a heterocycloalkyl ring.

65. The compound of claim 64 wherein said compound is 5-quinolin-6-ylmethylene-2-[(tetrahydro-thiopyran-4-ylmethyl)-amino]thiazol-4-one.

66. The compound of claim 64 where said compound is 5-quinolin-6-ylmethylene-2-[(tetrahydro-pyran-4-ylmethyl)-amino]-thiazol-4-one.

67. The compound of claim 64 where said compound is 2-[(1,1-dioxo-tetrahydro-thiopyran-4-ylmethyl)-amino]-5-quinolin-6-ylmethylene-thiazol-4-one.

68. The compound of claim 59 where

is a heteroaromatic ring.

69. The compound of claim 68 where said ring contains from one to two sulfur atoms as the only hetero atoms in the ring.

70. The compound of claim 69 where said compound is 2[(thiophen-2-ylmethyl)-amino]-5-[1-quinolin-6-yl-meth-(Z)-ylidene]-thiazol-4-one.

71. The compound of claim 69 wherein said compound is 2-(2-thiophen-2-yl-ethylamino)-5-[1-quinolin-6-yl-meth-(Z)-ylidene]-thiazol-4-one.

72. The compound of claim 69 wherein said compound is 2-(1-thiophen-2-yl-ethylamino)-5-[1-quinolin-6-yl-meth-(Z)-ylidene]-thiazol-4-one.

73. The compound of claim 69 wherein said compound is 2-[(3-methyl-thiophen-2-ylmethyl)-amino]-5-quinolin-6-yl-meth-(Z)-ylidine-thiazol-4-one.

74. The compound of claim 68 wherein the ring contains from 1 to 2 nitrogen atoms as the only hetero atoms.

75. The compound of claim 74 wherein said compound is 2-(2-pyridin-3-yl-ethylamino)-5-[1-quinolin-6-yl-meth-(Z)-ylidene]-thiazol-4-one.

76. The compound of claim 74 wherein said compound is 2-[(pyridin-2-ylmethyl)-amino]-5-[1-quinolin-6-yl-meth-(Z)-ylidene]-thiazol-4-one.

77. The compound of claim 74 wherein said compound is 2-(2-pyridin-4-yl-ethylamino)-5-[1-quinolin-6-yl-meth-(Z)-ylidene]-thiazol-4-one.

78. The compound of claim 74 wherein said compound is 2-[2-(3H-imidazol-4-yl)-ethylamino]-5-[1-quinolin-6-yl-meth-(Z)-ylidene]-thiazol-4-one.

79. The compound of claim 68 wherein the ring contains at last one oxygen hetero atom.

80. The compound of claim 79 wherein said compound is 2-[(furan-2-ylmethyl)-amino]-5-[1-quinolin-6-yl-meth-(Z)-ylidene]-thiazol-4-one.

81. The compound of claim 58 wherein X is hydroxyloweralkylene.

82. The compound of claim 81 wherein

is a heteroaromatic ring.

83. The compound of claim 82 wherein said compound is 2-(2-hydroxy-1-thiophen-2-yl-ethylamino)-5-[1-quinolin-6-yl-meth-(Z)-ylidene]-thiazol-4-one.

84. The compound of claim 81 wherein

is a cyclolower alkyl.

85. The compound of claim 84 wherein said compound is 2-1-cyclohexyl-2-hydroxy-ethylamino)-5-[1-quinolin-6-yl-meth-(Z)-ylidene]-thiazol-4-one.

86. The compound of claim 58 wherein X is selected from amino substituted lower alkylene, mono- or di-lower amino substituted lower alkylene, and imido substituted lower alkylene.

87. The compound of claim 86 wherein

is heteroaromatic ring.

88. The compound of claim 87 wherein said compound is N-(4-oxo-5-quinolin-6-ylmethylene-4,5-dihydro-thiazol-2-yl)-thiophene-2-carboxamidine.

89. The compound of claim 58 wherein X is halo lower alkylene.

90. The compound of claim 89 wherein

is heteroaromatic ring.

91. The compound of claim 90 wherein said compound is 2-(2,2-difluoro-2-pyridin-2-yl-ethylamino)-5-[1-quinolin-6-yl-meth-(Z)-ylidene]-thiazol-4-one hydrochloride.

92. The compound of claim 90 wherein said compound is 2-[2,2-difluoro-2-(1-oxy-pyridin-2-yl)-ethylamino]-5-[1-quinolin-6-yl-meth-(Z)-ylidene]-thiazol-4-one.

93. The compound of claim 58 wherein X is phenylloweralkylene.

94. The compound of claim 93 wherein

is a 5 or 6 membered heterocycloalkyl ring.

95. The compound of claim 94 wherein said compound is 2-(2-morpholin-4-yl-2-phenyl-ethylamino)-5-[1-quinolin-6-yl-meth-(Z)-ylidene]-thiazol-4-one.

96. The compound of claim 58 wherein X is cycloloweralkylene.

97. The compound of claim 96 wherein said compound is 2-(2-phenyl-cyclopropylamino)-5-[1-quinolin-6-yl-meth-(Z)-ylidene]-thiazol-4-one.

98. The compound of claim 1 wherein said compound has the formula:

I-F

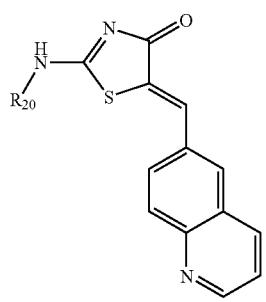

wherein $R_{20}$ is

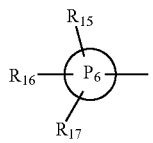

is a carbon containing ring attached through its carbon atom, which ring is selected from a 4 to 6 membered heterocycloalkyl ring containing from 3 to 4 carbon atoms and from 1 to 2 hetero atoms, nitrogen and sulfur, and a 5 to 6 membered heteroaromatic ring, wherein the heteroaromatic and heterocycloalky ring contain from 1 to 2 hetero atoms selected from oxygen, sulfur and nitrogen;

$R_{15}$, $R_{16}$ and $R_{17}$ are independently selected from hydroxy, $SO_2CH_3$, hydroxy-lower alkyl, hydrogen, lower alkyl, halogen, lower alkoxy, amino, mono- or di-lower alkyl amino, or when two of the substituents $R_5$, $R_6$ and $R_7$ are substituted on adjacent carbon atoms on ring

, these two substituents can be taken together with their adjacent, attached carbon atoms to form a group selected from an aryl ring, a 3 to 6 membered cyclic lower alkyl ring, a 4 to 6 membered heterocycloalkyl ring and a 4 to 6 membered heteroaromatic ring, said heterocycloalkyl ring and said heteroaromatic ring containing from 1 to 2 hetero atoms selected from oxygen, nitrogen and sulfur; or N-oxides of compounds where $R_{20}$ contains a nitrogen in the heterocycloalkyl ring or heteroaromatic ring, sulfones where $R_{20}$ contains a sulfur in the heterocycloalkyl ring; or pharmaceutically acceptable salts thereof.

99. The compound of claim 98 wherein $R_{20}$ is a heteroaromatic ring containing two hetero atoms.

100. The compound of claim 99 wherein said compound is 2-(thiazol-2-ylamino)-5-[1-quinolin-6-yl-meth-(Z)-ylidene]-thiazol-4-one.

* * * * *

UNITED STATES PATENT AND TRADEMARK OFFICE
CERTIFICATE OF CORRECTION

PATENT NO. : 7,326,786 B2  Page 1 of 1
APPLICATION NO. : 11/170300
DATED : February 5, 2008
INVENTOR(S) : Li Chen and Shaoqing Chen It is certified that error appears in the above-identified patent and that said Letters Patent is hereby corrected as shown below:

Column 59, Claim 39, line 6, delete "nitrogen" and insert
-- sulfur --.

Signed and Sealed this

Twenty-fourth Day of March, 2009

JOHN DOLL
*Acting Director of the United States Patent and Trademark Office*